US007662939B1

(12) United States Patent
Romero et al.

(10) Patent No.: US 7,662,939 B1
(45) Date of Patent: Feb. 16, 2010

(54) MOLECULAR DETERMINANTS OF TROPISM AND VIRULENCE IN ENTEROVIRUSES

(75) Inventors: Jose R. Romero, Omaha, NE (US); Shelton S. Bradrick, Omaha, NE (US); James J. Dunn, Omaha, NE (US)

(73) Assignee: Board of Regents of the University of Nebraska, Omaha, NE (US)

( * ) Notice: Subject to any disclaimer, the term of this patent is extended or adjusted under 35 U.S.C. 154(b) by 478 days.

(21) Appl. No.: 10/048,709

(22) PCT Filed: Jul. 8, 2000

(86) PCT No.: PCT/US00/18681

§ 371 (c)(1), (2), (4) Date: Jun. 10, 2002

(87) PCT Pub. No.: WO01/04136

PCT Pub. Date: Jan. 18, 2001

Related U.S. Application Data

(60) Provisional application No. 60/143,104, filed on Jul. 9, 1999.

(51) Int. Cl.
*C07H 21/02* (2006.01)
*C12N 15/00* (2006.01)
*C12N 7/04* (2006.01)
*C12N 7/01* (2006.01)

(52) U.S. Cl. .................... 536/23.1; 435/320.1; 435/236; 435/235.1

(58) Field of Classification Search ........................ None
See application file for complete search history.

(56) References Cited

U.S. PATENT DOCUMENTS 6,071,742 A 6/2000 Tracy et al.

FOREIGN PATENT DOCUMENTS

WO       WO98/39426       9/1998

OTHER PUBLICATIONS

Melnick, J. "Enteroviruses: Polioviruses, Coxsackieviruses, Echoviruses, and Newer Enteroviruses" Fields Virology, Third Edition, edited by B.N. Fields, D. M. Knipe, P. M. Howley, et al. Lippincott-Raven Publishers, Philadelphia, 1996.*
Caggana et al. " Identification of a single amino acid residue in the capsid protein VP1 of coxsackievirus B4 that determines the virulent phenotype". J. Virology 67, 4797-4803, 1993.*
Lee et al. Genomic regions of coxsackievirus B3 associated with cardiovirulence J. Med. Virol. 52: 341-347, 1997. as listed on the IDS filed on Jun. 10, 2002.*
Chapman et al. "Sites other than nucleotide 234 determine cardiovirulence in natural isolates of coxsackievirus B3." J. Med. Virology 52:258-261, 1997, as listed on the IDS filed on Jun. 10, 2002.*
Rinehart et al. "Molecular determinants for virulence in coxsackievirus B1 infection." J. Virol. 71(5):3986-3991, 1997, cited in IDS.*
Kandolf R, et al. "Mechanisms and consequences of enterovirus persistence in cardiac myocytes and cells of the immune system." Virus Res. Aug. 1999;62(2):149-58.*
Gauntt CJ, et al. "Molecular mimicry, anti-coxsackievirus B3 neutralizing monoclonal antibodies, and myocarditis." J Immunol. Mar. 15, 1995;154(6):2983-95.*
Alexander, et al., "Poliovirus containing picornaviridae type 1 and/or type 2 internal ribosomal entry site elements: genetic hybrids and the expression of a foreign gene", *Proc. Natl. Acad. Sci. USA*, 1994, 91, 1406-1410.
Cameron-Wilson, C.L. et al. "Nucleotide sequence of an attenuated mutant of coxsackievirus compared with the cardiovirulent wildtype:assessment of candidate mutations by analysis of a revertant to cardiovirulence", *Clin. Diagn. Virol.*, 1998, 9, 99-105.
Chapman, N.M. et al. "Sites other than nucleotide 234 determine cardiovirulence in natural isolates of coxsackievirus B3", *J. Med. Virol*, 1997, 52, 258-261.
Gauntt, C.J. et al., "Coxsackievirus B3 clinical isolates and murine myocarditis", *Virus Res*, 1996, 41, 89-99.
Gromeier, et al., "Dual stem loops within the poliovirus internal ribosomal entry site control neurovirulence", *J. Virol*, 1999, 73, 958-964.
Ishii, et al., "A new internal ribosomal entry side 5' boundary is required for poliovirus translation initiation in mouse system", *J. Virol*, 1998, 72, 2398-2405.
Knowlton, K.U. et al., "A Mutation in the puff region of VP2 attenuates the myocardtic phenotype of an infections cDNA of the Woodruff variant of coxsackievirus B3", *J. Virol*, 1996, 70,7811-7818.
Lee, et al., "Genomic regions of coxsackievirus B3 associated with cardiovirulence", *.J.Med. Virol*, 1997, 52, 341-347.
Minor, P.D. "The molecular biology of poliovaccines", *Jrl. of Gen. Virol.*, 1992, 73, 3065-3077.
Rinehart, J.E. et al., "Molecular determinants for virulence in coxsackievirus B1 infection", *J. Virol*, 1997, 71, 3986-3991.
Romero, J.R. et al., "Sequence analysis of the downstream 5' nontranslated region of seven echoviruses with different neurovirulence phenotypes", *J. Virol*, 1995, 69, 1370-1375.
Romero, J.R. et al., Genetic divergence among the group B coxsackieviruses *The Coxsackie B Viruses*, 1997, 97-152.

(Continued)

*Primary Examiner*—Bo Peng
(74) *Attorney, Agent, or Firm*—Dann, Dorfman, Herrell & Skillman; Robert C. Netter, Jr.

(57) ABSTRACT

Recombinant enteroviruses for use as vaccines or vectors, which are modified in tropism or virulence, are disclosed. Also disclosed are DNA constructs comprising enterovirus-derived molecular determinants of tropism or virulence for use in targeting genes of interest to specific cells or tissues. The recombinant enteroviruses and DNA constructs comprise molecular determinants of tropism and virulence localized in specific domains of the 5'NTR of the enteroviral genome.

10 Claims, 7 Drawing Sheets

OTHER PUBLICATIONS

Shiroki, K. et al., Host range phenotype induced by mutations in the internal ribosomal entry site of poliovirus RNA, *J. Virol*, 1997, 71, 1-8.

Tu, et al., "The cardiovirulent phenotype of coxsackievirus B3 is determined at a single site in the genomic 5' nontranslated region", *J. Virol*, 1995, 69(8), 4607-4618.

Tracy, S.M. et al., "Phenotypic and genotypic differences among naturally occurring coxsackie virus B3 variants", *Eur. Heart J.*, 1987, 8, 445-448.

Zhang, H.Y. et al., "Attenuation of a reactivated cariovirulent coxsackievirus B3: the 5'-nontranslated region does not contain major attenutaion determinants", *J. Med. Virol.*, 1993, 41, 129-137.

\* cited by examiner

| Virus | 5'—NTR—CAPSID—NON-STRUCTURAL—NTR—3' | Myocarditis lesion score | Cardiac viral titer |
|---|---|---|---|
| 20 | | 3.8 ± 0.2 | 5.9 ± 1.4 |
| CO | | 0 | n.d. |
| AS | | 2.2 ± 0.4 | 7.7 ± 0.6 |
| COP1/20 | | 3.4 ± 0.2 | 4.2 ± 1.1 |
| CO5'/20 | | 0 | n.d. |
| CO5'P1/20 | | 0 | n.d. |
| ASP1/20 | | 3.0 ± 0.5 | 6.6 ± 1.5 |
| AS5'/20 | | 2.0 ± 0.4 | 3.9 ± 1.0 |
| AS5'P1/20 | | 3.8 ± 0.2 | 8.7 ± 0.1 |

Figure 5

```
              90                                    120
              |                                      |
CVB3/20  -tacccccctcccccaactgtaacttagaagtaac----acacaccgatcaacag
CVB3/AS  -agt    t t       tc            c    ----       t       t
CVB3/CO  ca tt           ttctt   a              c  gcaag t aga   g  g 150                      180
                           |                        |
CVB3/20  tcagcgtggcacaccagccacgttttgatcaagcacttctgttac
CVB3/AS  t         a       t          g
CVB3/CO  g ga aca   a      tgt   c a c              g
```

Figure 7

SEQUENCE LISTING

<160> NUMBER OF SEQ ID NOS: 7

<210> SEQ ID NO 1
<211> LENGTH: 744
<212> TYPE: RNA
<213> ORGANISM: Coxsackievirus B3

<400> SEQUENCE: 1

```
uuaaaacagc cuguggguug aucccaccca caggcccauu gggcgcuagc acucugguau      60
cacgguaccu uugugcgccu guuuuauacc cccucccca acuguaacuu agaaguaaca     120
cacaccgauc aacagucagc guggcacacc agccacguuu ugaucaagca cuucuguuac     180
cccggacuga guaucaauag acugcucacg cgguugaagg agaaagcguu cguuauccgg     240
ccaacuacuu cgaaaaaccu aguaacaccg uggaaguugc agaguguuuc gcucagcacu     300
accccagugu agaucagguc gaugagucac cgcauucccc acgggcgacc guggcggugg     360
cugcguuggc ggccugccca uggggaaacc caugggacgc ucuaauacag acauggugcg     420
aagagucuau ugagcuaguu gguaguccuc cggcccuga augcggcuaa uccuaacugc     480
ggagcacaca cccucaagcc agagggcagu gugucguaac gggcaacucu gcagcggaac     540
cgacuacuuu ggguguccgu guuucauuuu auuccuauac uggcugcuua uggugacaau     600
ugagagaucg uuaccauaua gcuauuggau uggccauccg gugacuaaua gagcuauuau     660
auaucccuuu guugggguuua uaccacuuag cuugaaagag guuaaaacau uacaauucau     720
uguuaaguug aauacagcaa aaug                                           744
```

-continued

<210> SEQ ID NO 2
<211> LENGTH: 645
<212> TYPE: RNA
<213> ORGANISM: Echovirus 12

<400> SEQUENCE: 2
uuaaaacagc cugugggung uccccaccca cagggcccac ugggcgcuac acacugguau    60
cccgguaccu uugugcgccu guuuuauaua cccucccccuc aguaaccuag aaguucauca   120
caaaugauca auaguuagcu caacaaacca guugagccua gaucaagcac uucuguuacc   180
ccgggcugag uaucaauaag cuguugacac ggcugaagga gaaaacgccc guuacccgac   240
cagcuacuuc ggagaaccua guaucaccau agagguugcg uagcguuucg cuccgcacaa   300
ccccagugua gaucaggucg augagucacc gcguucccca caggcgacug uggcgguggc   360
ugcguuggcg gccugcccau gggguuaccc auggggacgcu ucaauacuga cauggugugu   420
agaguugacu gagcuagcug guaguccuccg ggccccugaa ugcggcuaau ccaacugug    480 gagcaagugc ccacaaccca gugggugggcu ugucguaaug ggcaacucug cagcggaacc   540
gacuacuuug ggugaccgug uuucucuuua uucuuauauu ggcugcuuau ggugacaauc   600
ucagaguugu uaccauauag cuauugguuu ggccaaccag ugacu                   645

<210> SEQ ID NO 3
<211> LENGTH: 94
<212> TYPE: RNA
<213> ORGANISM: Coxsackievirus B3

<400> SEQUENCE: 3
uacccccucc cccaacugua acuuagaagu aacacacacc gaucaacagu cagcguggca    60
caccagccac guuuugauca agcacuucug uuac                                94

<210> SEQ ID NO 4
<211> LENGTH: 94
<212> TYPE: RNA
<213> ORGANISM: Coxsackievirus B3

<400> SEQUENCE: 4
agucccuuuc cccaaucgua acuuagaagc aacacacacu gaucaauagu uagcguggca    60
aaccagcuac guuuugaucg agcacuucug uuac                                94

<210> SEQ ID NO 5
<211> LENGTH: 99
<212> TYPE: RNA
<213> ORGANISM: Coxsackievirus B3

<400> SEQUENCE: 5
caauucccuc ccuucuuuga aacuuagaag caagcaagau aagacggucg acaggcgaca    60 cagcaaaacca gcuguguucua gaccaagcac uucugugac                         99

<210> SEQ ID NO 6
<211> LENGTH: 654
<212> TYPE: DNA
<213> ORGANISM: Coxsackievirus B3

```
<400> SEQUENCE: 6 agtcccttc  cccaatcgta  acttagaagc  aacacacact  gatcaatagt  tagcgtggca       60
aaccagctac  gttttgatcg  agcacttctg  ttaccccgga  ctgagtatca  atagactgct      120
agcgcggttg  aaggagaaaa  cgttcgttat  ccggccaact  acttcgagaa  acctagtaac      180
accatggaag  ttgcagagtg  tttcgctcag  cactacccca  gtgtagatca  ggtcgatgag      240
tcaccgcatt  ccccacgggc  gaccgtggcg  gtggctgcgt  tggcggcctg  cccatgggaa      300
acccatggga  cgctcttata  cagacatggt  gcgaagagtc  tattgagcta  gttggtattc      360
ctccggcccc  tgaatgcggc  taatcctaac  tgtggatcat  gcgccctcaa  accagaggga      420
agcgtgtcgt  aatgggcaac  tccgcagcgg  aaccgactac  tttgggtgtc  cgtgtttcat      480
tttattctta  ctttggctgc  ttatggtgac  aattgaaagg  ttgttaccat  atagctattg      540
gattggccat  ccggtgacaa  acagagctat  catatatctc  ttcgtagggt  ttgtaccact      600
tagcttgaaa  gaggtcaaga  cattgcaatt  cattatccaa  ttgaacacag  caaa            654

<210> SEQ ID NO 7
<211> LENGTH: 660
<212> TYPE: DNA
<213> ORGANISM: Coxsackievirus B3

<400> SEQUENCE: 7
caattccctc  ccttctttga  aacttagaag  caagcaagat  aagacggtcg  acaggcgaca       60
cagcaaacca  gctgtgtcta  gaccaagcac  ttctgtgacc  ccggactgag  tatcaatagg      120
ctgctcgcgc  ggctgaagga  gaaaccgtcc  gttatccggc  caactacttc  gagaaaccca      180
gtaacatcat  ggacgttgca  gagcgtttcg  ctcaacactt  ccccgtgta   gatcaggtcg      240 atgagtcacc  gctttcccca  cgggcgaccg  tggcggtggc  tgcgttggcg  gcctgcctgt      300 ggggcaccc   acaggacgct  ctaatacaga  catggtgcga  agagtctatt  gagctagttg      360
gtagtcctcc  ggcccctgaa  tgcggctaat  cctaactgcg  gagcatgcac  ccacaagcca      420
gtgggtagcg  tgtcgtaacg  ggcaactctg  cagcggaacc  gactactttg  ggtgaccgtg      480
tttcttttta  ttctctcatt  ggctgcttat  ggtgacaatt  gaggaattgt  taccatatag      540
ctattggatt  ggccatccgg  tgtctaacag  agcaattgtt  tatctgtttg  tcggctttgt      600
gtctttgaac  ttcaagaatt  ataaaactct  cgacttcata  ctagagttaa  actcaataag      660
```

MOLECULAR DETERMINANTS OF TROPISM AND VIRULENCE IN ENTEROVIRUSES

This application claims priority to U.S. Provisional Application No. 60/143,104, filed Jul. 9, 1999, the entirety of which is incorporated by reference herein.

FIELD OF THE INVENTION

The present invention relates generally to the fields of molecular biology and virology. More specifically, the invention provides enteroviruses for use as vaccines or vectors, which are modified in tropism or virulence, as well as DNA constructs comprising enterovirus-derived molecular determinants of tropism or virulence for use in targeting genes of interest to specific cells or tissues.

BACKGROUND OF THE INVENTION

Several scientific and patent publications are referenced in this patent application to describe the state of the art to which the invention pertains. Each of these publications is incorporated by reference herein, in its entirety.

The family Picornaviridae includes at least five genera: cardiovirus, aphthovirus, enterovirus, rhinovirus, hepatovirus and a possibly a newly proposed genus paraenterovirus. The genus enterovirus (EV) is subdivided into five groups: the polioviruses (PV), coxsackieviruses groups A (CVA) and B (CVB), echoviruses (ECV) and the numbered EV.

The picornaviral genome is a single stranded, positive sense RNA molecule approximately 7,500 to 8,300 nucleotides (nts) in length. The genome is organized into a 5' nontranslated region (5'NTR), a polyprotein-coding region, a 3'NTR, and a terminal poly A tract. In all picornaviridae a small protein, VPg, is covalently bound to the 5' terminal-pUpUp of the genome. The viral coding region can be subdivided into the P1, P2 and P3 regions. In the non-human picornaviridae (cardio- and aphthovirus) the P1 region is preceded by an "L" region that encodes for a L proteinase. The P1 region encodes the four capsid proteins (VP14), while the P2 and P3 regions encode seven nonstructural proteins essential for the picornavirus life-cycle.

Picornaviridae 5' Nontranslated Region. The 5'NTR of the sequenced enteroviruses (EV) is remarkably constant in size (711-747 nts). Sequence analysis has demonstrated the existence of multiple regions of highly conserved nucleotide identity. Multiple stem-loop (SL) structures (or domains) exist within this region of the genome. Additionally, there is evidence for the existence of tertiary structural elements (pseudoknots) within the EV 5'NTR. Similarly, for the hepatoviruses and non-human picornaviridae (cardio- and aphthovirus) conserved secondary structures have also been predicted to exist within the 5'NTR.

Studies of PV 1-3, CVB 1 and, most recently, CVB 3 have demonstrated that the 5'NTR contains genomic elements necessary for replication, translation, and determinants of virulence. The initial 98 nucleotides (nts) of the 5'NTR from PV have been demonstrated to play a role in viral RNA replication. A ribonucleoprotein (RNP) complex at the 5' end of the PV NTR has been shown to be important for RNA replication. This RNP complex comprises the initial 98 nts of the 5'NTR (which fold into cloverleaf-like structure), the viral protein 3CD, and poly C binding protein 2 (PCBP2). For the other human picornaviridae a similar folding motif is predicted for the initial 84-98 nts.

The existence of a cis-acting genomic element within the 5'NTR of PV, in conjunction with trans-acting cellular proteins, is required for efficient translation of the protein coding region. This element, termed the internal ribosome entry site (IRES), is a discontinuous region spanning approximately from nts 140 to 620 of the PV 5'NTR. Evidence for the requirement of SLs II, IV, V and VI in PV translation has been provided. Stem-loop III has been proven to be nonessential for cap-independent translation. For representatives from each of the genera of the picornavirus family, a region of approximately 450 nts within the 5'NTR is required for cap-independent internal initiation of protein synthesis. Studies focusing on the downstream portion of the IRES have identified specific sequences and/or higher order structures that directly influence the ability of the PV IRES to efficiently initiate translation.

Picornaviridae tissue and species tropism. A major determinant of tissue and species tropism for the picornaviridae is the presence or absence of a viral receptor on the cell surface. For the picornaviridae this has been best studied for the PV. Poliovirus has a distinct species and tissue tropism, infecting only primates. In primates PV has a restricted tissue tropism; replicating only in pharynx, gut and neurons within certain regions of the central nervous system. However, PV has been shown to bind to tissues that do not support PV replication. Additionally, poliovirus receptor (PVR) RNA and protein has been shown to be expressed in tissues that are not sites of PV replication. These and other findings indicate that PV tissue tropism is not governed solely by the presence of the PVR in tissues.

Evidence is beginning to accumulate that viral 5'NTR-host protein interactions may be the level at which restriction of picornavirus species and tissue tropism occurs. The strongest support for the role of 5'NTR-cellular interactions as determinants of host range restriction comes from work by Shiroki et al. (J. Virol. 71: 1-8, 1997). PV1 (Mahoney strain) mutants within SLII at nts 128-134 were found to replicate well in primate cells but not in murine cells of TgPVR mice. SLII mutants demonstrated high neurovirulence in monkeys and low neurovirulence in mice. The IRES dependent translation of the SLII mutants was found to be blocked in Tg mouse kidney cells (TgSVA) and mouse neuroblastoma cells (NS20Y) but not in HeLa cells. A follow-up study showed that SLII mutation revertants that recovered IRES function in a TgSVA cell-free translation system also recovered neurovirulence in mice (Ishii et al., J. Virol. 72: 2398-2405, 1998). These studies strongly suggest that an additional determinant of species or host range tropism is the interaction between the IRES and host factor(s). This restriction may be the result of host-restricted expression PV IRES function. These studies were performed using artificially altered 5'NTRs and therefore may not reflect the actual events that occur naturally. Evidence for host/tissue range restriction in a naturally-occurring picornavirus secondary to the IRES heretofore has not been available.

Virulence of CVB and other Picornaviruses. The group B coxsackieviruses (CVB) are responsible for a myriad of clinical syndromes involving almost every organ system that range from febrile exanthems to myocarditis and meningoencephalitis. It is widely accepted that the CVB are a major, if not the predominant, cause of viral myocarditis in humans. However, it is not yet know what elements of the CVB determine their ability to cause diseases in humans.

The enteroviral capsid has been shown to contain determinants contributing to the pathogenic phenotype of CVB4, CVB3, and the polioviruses (PVs). However, the sites determining the virulence phenotypes of these viruses do not colocalize to a single capsid region or even a single capsid protein. Determinants have been found in all four capsid proteins and are not necessarily located at surface-exposed residues of the virion.

For instance, a noncardiovirulent antibody escape mutant derived from the highly cardiovirulent CVB3/H3 strain was found to contain a single amino acid substitution (Asn3Asp) at position 165 of VP2 (Knowlton et al., J. Virol. 70: 7811-7818, 1996). When Asp165 was substituted for the Asn165 in VP2 of the parental cardiovirulent CVB3 strain, the myocarditic phenotype was significantly attenuated. Conversely, a change to Asn165 in VP2 of the antibody escape mutant reverted this strain to the cardiovirulent phenotype.

Specific nucleotide(s) within the 5'NTR are also known to alter the virulence phenotype of the PVs (reviewed by Minor, J. Gen. Virol. 73: 3065-3077, 1992), CVB1 (Rinehart et al., J. Virol. 71: 3986-3991, 1997), and CVB3 (Tu et al., J. Virol. 69: 4607-4618, 1995). A U→C mutation at nt 234 within the CVB3 5'NTR results in attenuation of the cardiovirulent phenotype in mice. Replacement of the cardiovirulent CVB3/M or CVB3/20 5'NTRs with that from CVB3/0 attenuates the resultant viruses for myocarditis (Tu et al., 1995, supra; Lee et al., J. Med. Virol. 52: 341-347, 1997). Subsequent analysis of multiple clinical CVB3 isolates as well as other enteroviruses demonstrated that nt 234 is always U regardless of the cardiovirulence phenotype of the virus, consistent with 234C being an artificial mutation.

Zhang et al. (J. Med. Virol. 41: 129-137, 1993) isolated an attenuated CVB3 strain (p14V1) following multiple passages of cardiovirulent CVB3/Nancy in human dermatofibroblasts. Sequence analysis of the 5'NTR revealed a single nucleotide change at position 690 (A→U). Insertion of 690U into the cardiovirulent parental virus did not alter the myocarditic phenotype, demonstrating that this mutation does not affect the cardiovirulence phenotype. Following passage of p14V1 in scid mice hearts, a revertant to cardiovirulence was isolated (Cameron-Wilson et al., Clin. Diagn. Virol. 9: 99-105, 1998). Sequence comparison of the 5'NTR and capsid coding region of this revertant to the attenuated p14V1 and cardiovirulent CVB3/Nancy strains suggested that amino acid 155 in VP1 might play a role in attenuation; however, this has not yet been demonstrated.

The studies of genomic determinants of virulence for the foregoing and the majority of enteroviruses have relied on strains engineered by physiochemical or biologic means in the laboratory. As a result, it remains undetermined whether the anomalies in the 5'NTRs of those strains are clinically relevant determinants of virulence, i.e., in naturally occurring EVs.

SUMMARY OF THE INVENTION

It has now been discovered in accordance with the present invention that molecular determinants of both tropism and virulence in enteroviruses are located in specific regions of the 5'NTR of the enteroviral genome. This discovery enables the preparation of modified enteroviruses for use as vaccines or vectors, which are restricted or otherwise altered in tropism or virulence, as well as DNA constructs comprising enterovirus-derived molecular determinants of tropism or virulence for use in targeting genes of interest to specific cells or tissues.

According to one aspect of the invention, an enterovirus genome for use as a vector or vaccine is provided. The genome is modified to produce a virus which is attenuated or which is restricted or altered in host range as compared with an equivalent, but unmodified genome. The modification comprises replacing a 5'NTR of the genome with a 5'NTR of an enterovirus genome that produces an avirulent or host range-restricted or altered enterovirus. In a preferred embodiment, the modification comprises replacing Domain I through Domain VII (the complete internal ribosomal entry site (IRES)) of the 5'NTR. More preferably, the modification comprises replacing domain I through Domain IV; and even more preferably, Domain II together with the linker between Domain I and Domain II of the 5'NTR is modified. The enterovirus genome preferably is from a virus selected from the group consisting of coxsackievirus, echovirus and poliovirus. More preferably, it is a coxsackievirus B3 or an echovirus 12.

According to another aspect of the invention, a vector for delivering a gene of interest to a target cell is provided. The target cell is a cell in which a selected enterovirus is capable of replication, and the vector comprises a 5'NTR of the selected enterovirus. Preferably, the enterovirus is selected from the group consisting of coxsackievirus, echovirus and poliovirus, and most preferably the enterovirus is a coxsackievirus B3. The target cell preferably is a human cell, more preferably a heart cell.

According to another aspect of the invention, a recombinant enterovirus is provided, having a genome in which part or all of the endogenous 5' NTR is replaced with an equivalent part or all of a heterologous 5'NTR of an enterovirus selected from the group consisting of coxsackievirus, poliovirus and echovirus. In one embodiment, the recombinant enterovirus is a poliovirus comprising a 5' NTR of an echovirus, preferably ECV12. In another embodiment, the recombinant enterovirus is a coxsackievirus comprising a 5'NTR of ECV 12.

In preferred embodiments, a portion of the endogenous 5'NTR comprising Domains I-VII is replaced with an equivalent portion of the heterologous 5' NTR. More preferably, a portion of the endogenous 5'NTR comprising Domain II together with a Domain I/II linker is replaced with an equivalent portion of the heterologous 5'NTR.

Other features and advantages of the present invention will be understood by reference to the detailed description of the invention and examples that follow.

BRIEF DESCRIPTION OF THE DRAWINGS

FIG. 5. Schematic representation, myocarditis lesion score and cardiac viral titer of CVB3 and intratypic chimeras. Myocarditis lesion scoring (see Example 2) and cardiac viral titers (log of $TCID_{50}$ per gram of heart tissue) are given as mean 6 standard error of the mean. n.d., no virus titer detected.

(FIG. 6A) Replication of cardiovirulent CVB3/20, noncardiovirulent CVB3/CO, and intratypic chimeras; (FIG. 6B) replication of cardiovirulent CVB3/20, CVB3/AS, and intratypic chimeras. Cells were inoculated as described in Example 2 and harvested by freezing at specific times shown. Virus titers were determined on HeLa cell monolayers. p.i., postinoculation.

FIG. 7. CVB3 SL I/II-SL II sequences and predicted secondary structure of three CVB3 clinical isolates: CVB3/20 (cardiovirulent), CVB3/AS (cardiovirulent) and CVB3/CO (non-cardiovirulent). The CVB3/20 5'NTR segment is SEQ ID NO:3; the CVB3/AS 5'NTR segment is SEQ ID NO:4; the CVB3/CO 5'NTR segment is SEQ ID NO:5.

DETAILED DESCRIPTION OF THE INVENTION

I. Definitions

Figure 1:
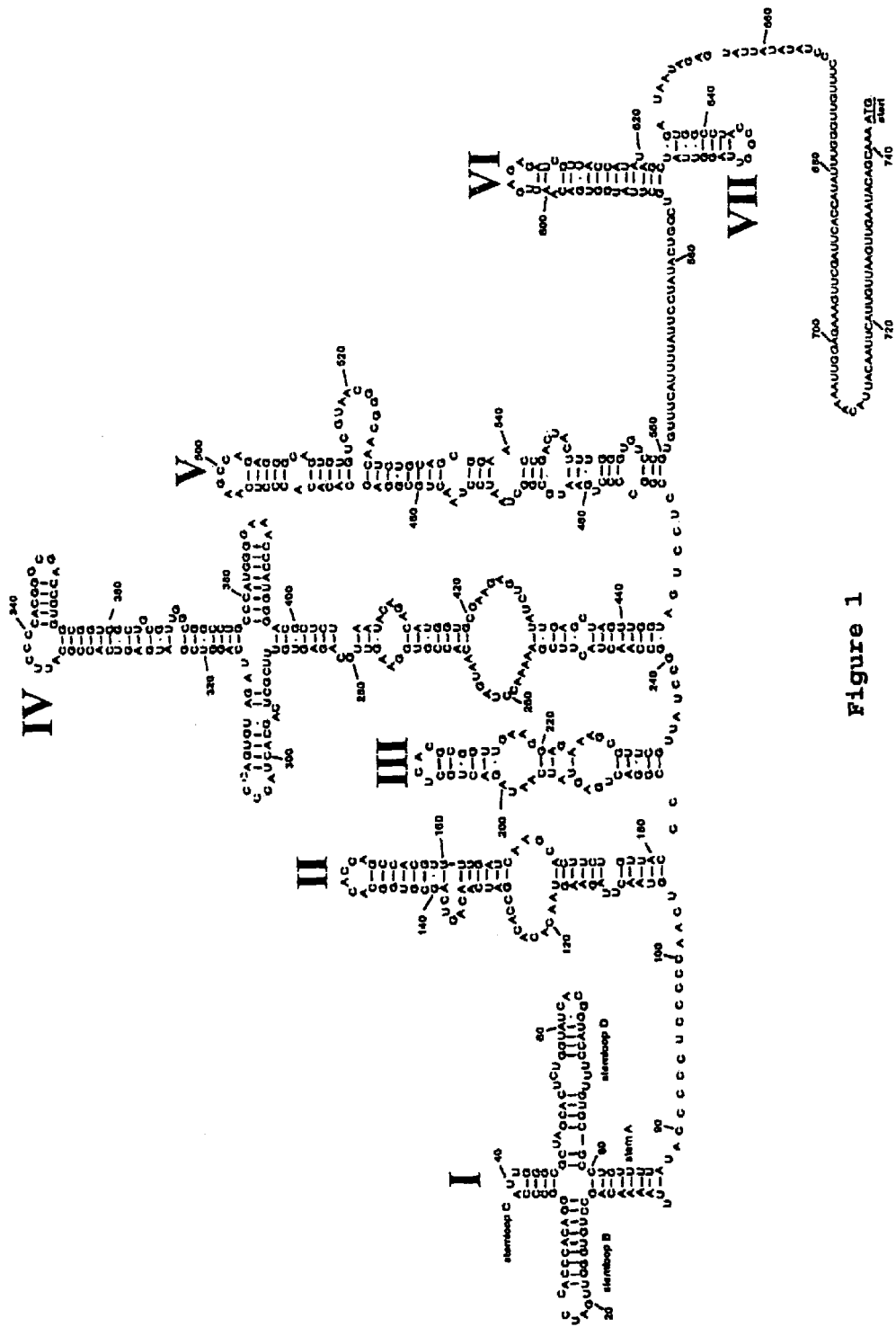
FIG. 1. Diagram (with sequence of SEQ ID NO:1) of the 5'NTR of CVB3 (numbering according to Tracy et al., Arch. Virol. 122: 398-409, 1992).

Certain aspects of the present invention employ conventional molecular biology, microbiology, and recombinant DNA techniques that are well known in the art. See, e.g., Sambrook et al., "Molecular Cloning: A Laboratory Manual (1989); or "Current Protocols in Molecular Biology", eds. Frederick M. Ausubel et al., John Wiley & Sons, 1999.

Therefore, if appearing herein, the following terms have the definitions set out below.

A "coding sequence" or "coding region" refers to a nucleic acid molecule having sequence information necessary to produce a gene product, when the sequence is expressed.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement other transcription control elements (e.g. enhancers) in an expression vector.

Transcriptional and translational control sequences are DNA regulatory sequences, such as promoters, enhancers, polyadenylation signals, terminators, and the like, that provide for the expression of a coding sequence in a host cell.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

A "vector" is a replicon, such as plasmid, phage, cosmid, or virus to which another nucleic acid segment may be operably inserted so as to bring about the replication or expression of the segment.

An "origin of replication" refers to those DNA sequences that participate in the in the initiation of DNA synthesis.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

A "heterologous" region of a nucleic acid construct is an identifiable segment of the nucleic acid molecule within a larger molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The terms set forth below, relating to the biological molecules and methods of the present invention, are used throughout the specifications and claims The term "attenuated" refers to a virus that is modified to be less virulent (disease-causing) than wildtype virus.

The term "tropism" refers to the ability of a virus to infect or colonize a particular organism or tissue. Two types of tropism are discussed herein. "Tissue tropism" refers to the differential ability of a particular virus or viral strain to infect one tissue type (e.g., heart), but not another (e.g., brain). "Species tropism" refers to the differential ability of a particular virus or viral strain to infect a particular species (e.g., humans) but not another (e.g., mice). Species tropism may also be referred to herein as "host range".

The term "cardiovirulent" refers to a virus that causes disease in the heart.

The term "noncardiovirulent" refers to a virus that causes substantially no disease in the heart. A formerly cardiovirulent virus that is attenuated may also be referred to herein as "noncardiovirulent" or "avirulent".

The term "open reading frame" refers to a length of RNA or DNA sequence, between a translation start signal (e.g., AUG or ATG) and any one or more of the known termination codons, which encodes one or more polypeptide sequences.

The term "5'NTR" or "5' untranslated (or nontranslated) region" refers to that portion of the EV genome to the 5' side of the coding region, which comprises transcriptional and translational regulatory elements.

The term "viral vector" refers to a virus that is able to transmit foreign or heterologous genetic information to a host. This foreign genetic information may be translated into a protein product, but this is not a necessary requirement for the foreign information.

The term "capsid coding region" refers to that region of a viral genome that contains the DNA or RNA code for protein subunits that are packaged into the protein coat of the virus particle.

II. DESCRIPTION

The 5'NTR of the EV is remarkably constant in size (711-747 nts). Sequence analysis has demonstrated the existence of multiple regions of highly conserved nucleotide identity. Moreover, phylogenetic comparisons, computer modeling of the available EV and rhinovirus 5'NTR sequences, and, in the case of some EV serotypes, nuclease mapping have demonstrated that the multiple stem-loop (SL) structures (or domains) within this region of the genome are very similar to one another. The similarity among these structures is illustrated by comparison of the CVB3 and ECV 5'NTRs shown in FIGS. 1 and 2, respectively.

Tissue and species tropism in the EV has been attributed to the interaction between one or more determinants on the viral capsid and cognate receptors on the cell surface. In addition, the capsid-receptor interaction has been hypothesized to determine other levels of strain-specific virulence, such as cardiopathy of certain strains of coxsackievirus B3 (CVB3). It has now been discovered in accordance with the present invention that the EV 5'NTR plays a significant role in both EV species/tissue tropism and strain-specific virulence. In particular, the region of the 5'NTR defined as "Domain II" or "stem-loop (SL) II" (see FIGS. 1 and 2), together with the linker between Domain I (SL I) and Domain II, comprise the most significant determinants of receptor-independent virulence and species/tissue tropism.

With respect to the first aspect of the invention, i.e., species/tissue tropism of the EV, it was heretofore known that the major determinant of species/tissue tropism for the best characterized of the enteroviruses, poliovirus (PV), exists at the level of the receptor. However, In vivo observations and mutational studies of the PV 5' nontranslated region (5'NTR) indicated that additional non-receptor determinants may reside within the 5'NTR. Thus far, post-entry viral determinants of tropism have not been identified in naturally occurring enteroviruses. Using coxsackievirus B3 (CVB3)-echovirus 12 (ECV12) recombinants, the inventors investigated non-receptor determinants of growth restriction on murine fetal heart fibroblasts (MFHF). A full length infectious chimera consisting of the ECV12 5'NTR in a CVB3-0 background (ECV12-0) was constructed. The recombinant virus was genetically stable and, similar to CVB3, was capable of replication in human and, to a lesser extent, simian cell lines. Unlike CVB3, however, ECV12-0 failed to replicate in MFHF's. To further investigate the ECV12 5' sequences responsible for MFHF growth restriction, ECV12/CVB3 intra 5'NTR chimeras were constructed. The inventors first learned that a chimera with ECV12 stem loops (SL) II-IV inserted into CVB3 was unable to replicate on MFHF whereas the converse chimera, ECV12 SL V-VII in CVB3, recovered growth on MFHF. In subsequent experiments it was determined that the specific region conferring the growth/no growth phenotype on MFHF was localized to the region comprising the linker between SL I and SL II (SL I linker) together with SL II. Thus, the ECV12 MFHF growth restriction phenotype localizes to this particular region of the 5'NTR. Mechanistically, these results indicate that the enteroviral 5'NTR serves as an additional determinant of species/tissue tropism via its role in viral translation and/or RNA replication. Certain of the experimental results leading to this discovery in accordance with the present invention are set forth in Example 1.

With respect to the second aspect of the invention, i.e., strain-specific virulence of certain EV, specifically CVB3, the CVB3 are known to cause myocarditis in humans and have been implicated in the pathogenesis of dilated cardiomyopathy. The molecular determinants of myocarditic phenotype for clinical isolates of CVB3 (as opposed to artificially generated variants) heretofore have been unknown. Using an established murine model of inflammatory heart disease, the inventors have shown that the homologous exchange of the 5'NTR of the infectious cDNA clone of the naturally occurring cardiovirulent CVB3/20 strain for that of the naturally occurring non-cardiovirulent CVB3/CO isolate completely attenuated the cardiovirulent phenotype of CVB3/20. In contrast, homologous exchange of the CVB3/20 capsid coding region for that of CVB3/CO did not alter the myocarditic phenotype of CVB3/20. These observations were expanded by examining the 5'NTR and capsid proteins of the cardiovirulent CVB3/AS clinical isolate. Recombinant viruses were generated in which the CVB3/AS 5'NTR, or the capsid coding region, or both, were used to replace homologous regions of CVB3/20. Each of the three chimeras retained the CVB3/20 cardiovirulent phenotype as evidenced by inflammatory lesions and significant viral titers in the myocardium. The data obtained from the CVB3/CO and AS chimeras indicate that the major determinant(s) of CVB3 cardiovirulence reside within the 5'NTR and, more particularly, within SL II of the 5'NTR together with the SL I/II linker. Computer modeling of this region in CVB3/CO (avirulence phenotype), CVB3/20 (virulence phenotype) and CVB3/AS (virulence phenotype) revealed few differences in the predicted folding pattern of the two virulent CVBs, but significant differences between the virulent CVBs and the avirulent CVB (See FIG. 7). Certain of the experimental results leading to this discovery in accordance with the present invention are set forth in Examples 2 and 3.

The unusually high sequence similarity among the EV 5'NTR enables corresponding regions of EV other than CVB3 or EV12 to be identified and utilized in accordance with the present invention. Specific examples of the region in which these determinants are located (i.e., SL II and the SL I/II linker) are shown in the table below (numbering is by comparison to the CVB3/20 genome sequence numbering shown in FIG. 1).

| Enterovirus | Region |
|---|---|
| CVB3/20 | nts 81-88 to 181-188 |
| CVB3/AS | nts 81-88 to 181-188 |
| CVB3/CO | nts 81-88 to 186-194 |
| ECV12 | nts 80-87 to 180-187 |
| PV | nts 81-88 to 191-198 |

Although the entire EV 5'NTR is considered suitable for use in the present invention, the upstream domains, i.e., SL I-IV are preferred for use, and SL II combined with the SL I/II linker is particularly preferred. Furthermore, although the CVB3 5'NTR and the ECV12 5'NTR are exemplified herein, this invention includes the 5'NTR and portions thereof of any EV. One of skill in the art would anticipate that, due to the high level of sequence and structural similarity among the EV 5'NTRs, that the tropism/virulence determinants identified in the exemplified EVs would likewise exist in the corresponding location in all EVs.

The identification of the SL II-SL I/II linker as a primary determinant of both species/tissue tropism and strain-specific virulence in the EV opens a wide range of applications in vaccine development, tissue targeting of vectors, and basic research into cellular events associated with the EV life cycle.

The discovery that specific features of the 5'NTR can determine virulence or avirulence of an EV can be used to advantage in development of anti-viral vaccines. For example, modified genomes of PV and CVB are used, or are being developed for use as live, attenuated viral vaccines (recombinant polioviruses are well known in the art; for coxsackieviruses, see, e.g., U.S. Pat. No. 6,071,742, co-pending U.S. application Ser. Nos. 09/403,672, 60/158,516 and PCT Application No. US99/07854, all to Tracy et al., incorporated by reference herein). These vaccines may be further attenuated by substituting a 5'NTR determinant (e.g., SL II-SL I/II linker) of a non-virulent viral strain, such as the non-cardiovirulent CVB3/CO, or another avirulent EV, such as ECV12. The more attenuating features possessed by a live viral vaccine, the lesser is the probability that the virus will revert to wild-type in the body, and the greater is its safety for clinical use.

Similarly, enteroviruses such as coxsackieviruses are being developed for use as viral vectors for the delivery of foreign genes of interest to target tissues in the body (recombinant polioviruses are well known in the art; for coxsackieviruses, see, e.g., U.S. Pat. No. 6,071,742, co-pending U.S. application Ser. Nos. 09/403,672, 60/158,516 and PCT Application No. US99/07854, all to Tracy et al.). Such vectors also may be further attenuated and therefore made more safe by substituting a non-virulent 5'NTR determinant for a corresponding virulence-conferring determinant.

In a particularly preferred embodiment, the 5'NTR, or a specific determinant thereof, of an avirulent or host range-restricted ECV, such as ECV12, is substituted for the 5' NTR of a virulent EV. This embodiment is preferred because certain ECV such as ECV12, while known to infect humans, do not appear to result in clinical disease. Thus, particularly attenuated recombinant EVs may be generated for use as vaccines or vectors. Particularly preferred are recombinant strains comprising ECV12 5'NTR attached to PV coding regions, and ECV12 5'NTR attached to CVB coding regions. Alternatively, the specific determinants of the ECV 5' NTR that confer the avirulence phenotype may be substituted for the corresponding region of a virulent EV (such as CVB or PV).

Alternatively, the species/tissue tropism/virulence determinants of the EV 5'NTR may be used in a homologous or heterologous vector to target cells of a selected species or tissue. For example, a vector comprising a gene of interest (reporter gene, therapeutic gene, etc.) operably linked to appropriate promoters and other expression controlling sequences, may further comprise a virulence domain of a cardiovirulent strain of CVB3 (e.g., CVB3/20 or CVB3/AS). Such a vector will then target the heart for delivery of the gene of interest.

The identification of a tropism/virulence determinant in the 5'NTR of the EV also provides a powerful research tool for identifying and characterizing cellular proteins that interact with EV in infected cells. As one example, model cellular systems may be developed that comprise a heterologous DNA construct containing the specific 5'NTR tropism/virulence determinant. Using established biochemical and molecular biological techniques, cellular proteins that bind to the determinant can be identified and isolated. Insight gained from such experimentation may be used to construct a model of the events involved in the EV life cycle within infected cells, and thereby to establish additional targets for therapeutic intervention with EV pathogenesis.

The information provided in the present invention can also be used for diagnostic purposes, e.g., to identify virulent, versus nonvirulent strains of an EV. For example, the SL II region of the non-cardiovirulent CVB3/CO strain differs from the cardiovirulent CVB/AS or CVB/20 strains by virtue of a 5-nucleotide insertion in the non-virulent determinant. Probes and primers for detecting differences in this and other regions of domain II may be developed, according to standard methods, to screen other CVB3 strains for cardiovirulence or nonvirulence.

The following examples are provided to describe the invention in greater detail. They are intended to illustrate, not to limit, the invention.

Example 1

Non-Receptor Determinants of Species and Tissue Tropism of the Enteroviruses

While animal models exist for the non-human picornaviridae, of the human picornaviridae only models for PV and CVB are available. The CVB are known to be capable of replicating in mice. This has led to the development of well characterized murine models for their study. The human and murine receptors for CVB 3 (hCAR and mCAR, respectively) are known. The majority of the echoviruses (ECV) do not replicate in murine cells or in mice. The definitive viral receptors for the majority of these viruses are unknown. The lack of a model system has hampered the study of host and tissue determinants for the ECV, CVA and numbered EV.

Phylogenetic analysis of the human picornaviridae has demonstrated that the ECV are more closely related to the CVB than they are to the PV. We have exploited this similarity to identify determinants of tissue and host range for the ECV. We selected ECV12 for study because, while it has been shown in-vivo to replicate in humans, it is not highly pathogenic. ECV12 also is not pathogenic for mice. In-vitro, ECV12 can replicate in some simian and human cell lines, but not in currently available murine cell lines. Taken together, these characteristics indicate that ECV12 exhibits species specificity which could be used to determine host/viral determinants of species/tissue restriction or tropism.

Unlike PV and CVB3 the definitive receptor for ECV12 is unknown. Therefore, the ability to study ECV12 growth in normally nonpermissive cells (due to receptor absence) by transfection induced expression of a viral receptor is not possible. However, because ECV12 and CVB3 share significant nucleotide identity within the 5'NTR (85% nucleotide identity within the IRES element), we reasoned that a chimera possessing the IRES and 5'NTR variable region of ECV12 fused with the CVB3 structural and nonstructural coding region could gain entry to cells normally permissive to CVB3 but nonpermissive to ECV12. Such a construct could permit the study of intracellular host cell/viral genome interactions.

Figure 3:
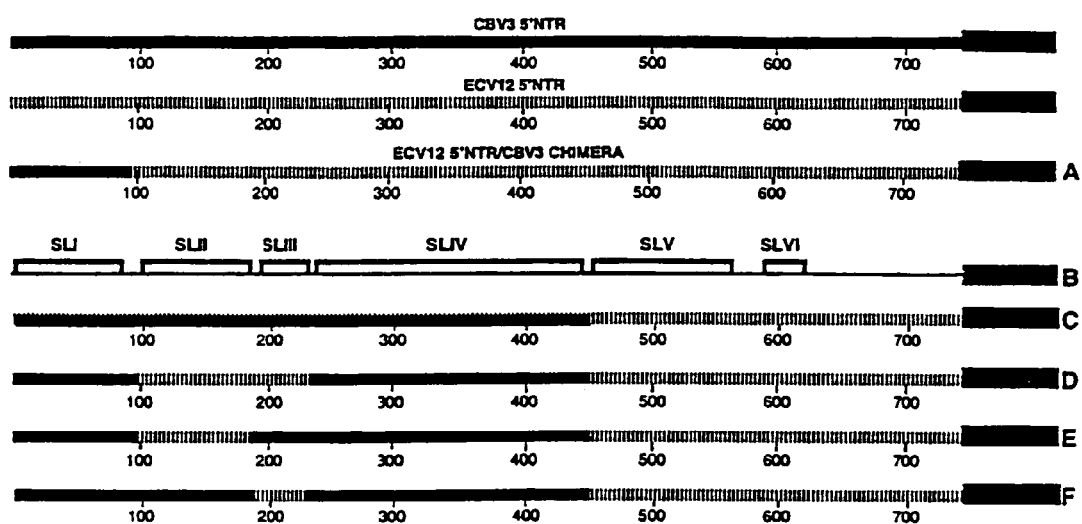
FIG. 3. Schematic representation of the stem-loop exchanges between the 5'NTRs of CVB3 and ECV12, to recover a murine growth phenotype (Example 1). Solid slim bar represents CVB3 5'NTR; broken slim bar represents ECV12 5'NTR, broad solid bars represent initial portions of capsid coding region for both viruses.

Because the 5'NTR "clover-leaf" structure of CVB3 and ECV12 are similar in structure, we focused on the role of the IRES as a possible additional determinant of species/tissue tropism. Using a high-fidelity RT-PCR assay, the 5'NTR of ECV 12 (Travis strain) was amplified, directly cycle sequenced, and cloned. Using a full-length infectious clone of CVB3 (CVB3-0. Chapman et al., Arch. Virol. 135: 115-130, 1994) we replaced nt 86 through the true initiation codon (nt 745) of CVB3 with the homologous region of ECV12. The resultant 5'NTR chimera, designated ECV12 5'NTR/CVB3 (FIG. 3) was found to be viable (Romero et al., Pediatric Research 41 (part 2): 129A, 1997).

The growth phenotype the chimera was compared to that of ECV12 and CVB3 using the LLMCK2 cell line. This cell line supports the replication of ECV12 and CVB3. Single cycle growth curves demonstrated that CVB3 had an eclipse period of 3 h while that of ECV12 was 4-5 h. Both viruses achieved peak titer at 10 h post-infection. The eclipse period of the ECV12 5'NTR/CVB3 chimera was found to be identical to that of ECV12. The chimera also reached peak titer at 10 h.

The ECV 12 5'NTR/CVB3 chimera offers several advantages for use in the study of nonreceptor determinants of viral/species-tissue tropism. First, the chimera possesses the SLI of CBV3. As such, there will not be the confounding variable of whether this SL can interact efficiently with the 3CD of CBV3 as would be the case if the SLI of ECV12 would have been used. Second, the construct encodes for the CBV3 capsid proteins. Virions packaging the chimeric genome will permit delivery of the ECV12 5'NTR into the cytoplasm of cells normally nonpermissive to ECV12 due to a lack of the specific receptor for it. Lastly, because murine models exist for CVB3, the chimera will permit the study of the effect of the ECV12 5'NTR in an in-vivo model system of pathogenesis.

Figure 4:
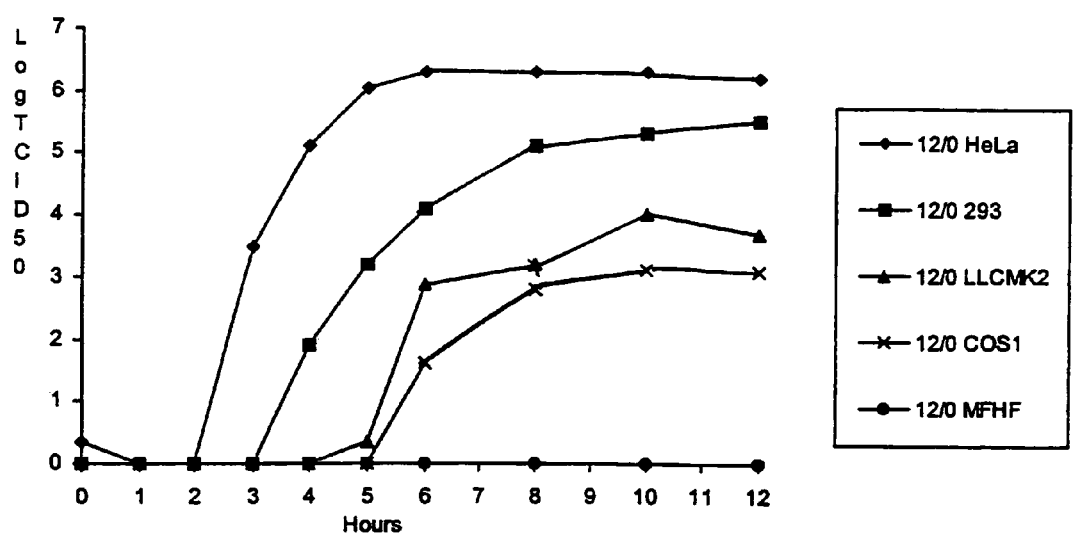
FIG. 4. Single cycle growth curve of CVB3, ECV12 and ECV12 5'NTR/CVB3.

We explored whether the chimera exhibited differential growth phenotypes on cell lines of human (HeLa, 293), simian (LLCMK2, Cos-1) or murine (MFHF) origin. The latter is derived from fetal mouse heart fibroblasts. We found that the ECV12 5'NTR/CVB3 chimera exhibited differences in growth phenotype that correlated with the origin of the cell line being tested (FIG. 4). The best viral growth kinetics were observed in cells of human origin. Intermediate growth kinetics were seen in simian-derived cells. Surprisingly, the chimera failed to replicate in the murine MFHF cells. Because the cell lines used support the growth of CVB3, the differences observed were not the result of receptor-mediated block to viral entry. As such, the differences represent differences in host protein/ECV 12 5'NTR interaction (s). This would suggest that, unlike in human and simian cells, the ECV125'NTR was not capable of effectively interacting with murine host proteins.

Figure 2:
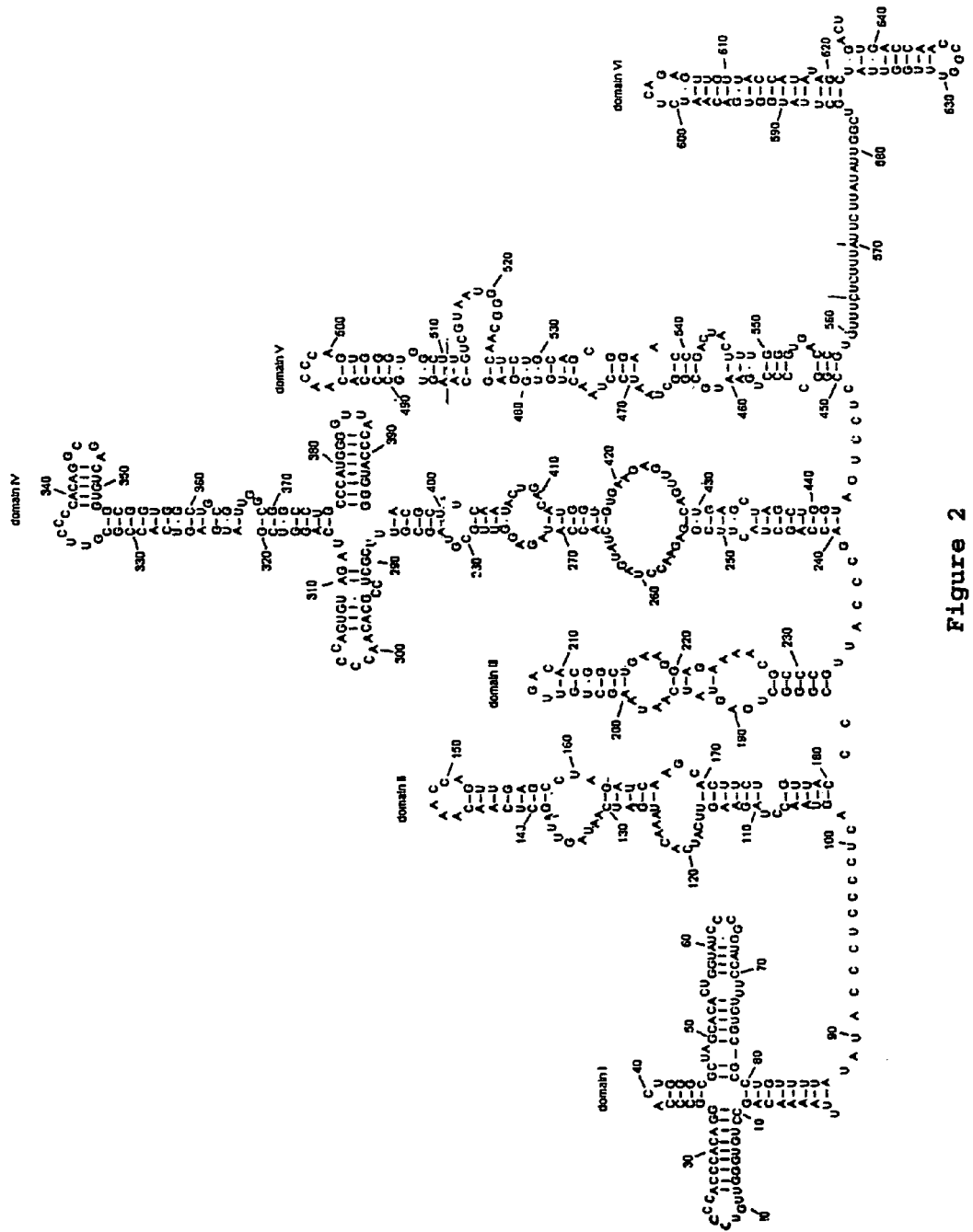
FIG. 2. Diagram (with sequence of SEQ ID NO:2) of Domains I-VII of the 5'NTR of ECV12.

We compared the CVB3 and ECV12 5'NTR sequences and predicted secondary structures to determine where differences existed among the two viruses. Interestingly, SLII was found to be the area in which the densest number of differences clustered (FIGS. 1 and 2). Relative to CVB3 these differences are as follows: the primary sequence of the CVB3 upstream 118-127 bulge varies at 6 of the 9 positions (ECV12 nts 116-125). While the primary sequence of the downstream 167-170 bulge is conserved, the bulge in ECV12 is composed of 3 rather than 4 nts (ECV12 nts 167-169). A uridine insertion exists in ECV12 upstream of CVB3 nt 128 that, together with two transitions, substantially alters the CVB3 128-133: 161-166 stem. In ECV12 the 5 nt 134-183 bulge of CVB3 is increased to 8 nts (ECV12 nts 131-138) with a corresponding downstream bulge of 3 nts (ECV nts 159-161) (positions 160-162 of CVB3). Although several differences occur within the most distal ECV12 stem 1339-145: 152-158 (CVB3 140-146: 153-159) the secondary structure is preserved. Within the SLII loop nt 148 of ECV 12 is A rather than C.

Although eight nt differences were found in SLE, no change in the predicted secondary structure occurred. The C at CVB3 nt 208 of the loop is G in ECV12. Twenty seven differences were observed within SLIV. The stem-bulge structure formed by CVB3 nts 269-288: 398-419 showed the most differences between the two viruses (ECV12 266-286: 396-417) The CVB3 proximal stem-bulge formed by nts 269-277: 407-419 in ECV12 has a one pair shorter stem and a bulge that is increased by 2 nts in ECV12 (nts 266-276: 405-417). The minor upstream 2 nt bulge at nts 280, 281 is increased to 3 nts in ECV12 (nts 280-282). The loop at positions CVB3 302-306 is increased by 2 nts (ECV12 nts 299-305). There is an A to G transition at nt 335 in the distal bulge.

Twelve differences are observed within SLV. The predicted secondary structure of SLV is preserved. Within the distal loop the G at position 499 is changed to C. Within the large bulge formed from nts 515-527 the C at nt 521 is changed to U (nt 519) in ECV12. The major changes found in SLVI lie within the loop where in CVB3 the unpaired sequence is 5'-GAGA-3'. In ECV12 unpaired sequence is two nts larger and has the sequence 5'-CUCAGA-3'.

Example 2

Genomic Determinants of Cardiovirulence in Coxsackievirus B3 Clinical Isolates

Localization to the 5' Nontranslated Region

The studies of genomic determinants of virulence for the majority of enteroviruses have relied on strains engineered by physiochemical or biologic means in the laboratory. This example describes the examination of the natural genetics of cardiovirulence in clinical CVB3 strains, using two phenotypically and genotypically distinct CVB3 clinical isolates. Utilizing reverse transcription-PCR (RT-PCR) to obtain the 5'NTR and P1 coding regions from CVB3/AS and CVB3/CO RNAs, we constructed intratypic chimeric viral genomes in the CVB3/20 background to test the hypothesis that these genomic regions encoded determinants of the viral cardiovirulent phenotype.

Materials and Methods

Cells and viruses. HeLa cells (American Type Culture Collection, Manassas, Va.) were maintained as monolayers in minimal essential medium (MEM) supplemented with 10% (vol/vol) fetal calf serum, 2 mM L-glutamine, 25.5 mM sodium bicarbonate, and 50 mg of gentamicin/ml. The complete sequence and characterization of the full-length infectious cDNA clone of CVB3/20 have been described previously (Tracy et al., Arch. Virol. 122: 398-409, 1992). The CVB3/AS and CVB3/CO strains were isolated from stool samples of patients with viral encephalitis. CVB3/AS was isolated from a 10-year-old male in 1977, and the CVB3/CO strain was isolated from a 5-year-old male in 1978. The cardiovirulence phenotypes of CVB3/AS and CVB3/CO have been defined previously in C3H/HeJ and CD-1 mice. Aliquots of low-passage viral stocks were obtained by inoculation of nearly confluent HeLa cell monolayers at a multiplicity of infection (MOI) of 0.5 to 150% tissue culture infective doses (TCID50) per cell and stored at −80° C.

Primers for RT-PCR and sequencing. The first nine bases of each of the primers used for the amplification and sequencing of naturally occurring CVB3 5' nontranslated and capsid coding regions are listed in Table 1.

TABLE 1

Primers used for the amplification and sequencing of CVB3

| Name | Length | Sequence (first 9 bases) | Location[a] | Orientation[b] |
|---|---|---|---|---|
| T1 | 20 | 5'-TCACTATAG-3' | 1 | S |
| JRp64 | 25 | 5'-ACGGTACCT-3' | 63 | S |
| JRp577 | 20 | 5'-TGGCTGCTT-3' | 582 | S |
| B3-CO/Sac I | 19 | 5'-GATGGGAGC-3' | 742 | S |
| JRpATG | 15 | 5'-TGAACTCGA-3' | 756 | A |
| B3-1226-CC | 29 | 5'-GGGCAAAAC-3' | 1226 | S |
| B3-1464 | 20 | 5'-GTGTATAAY-3' | 1464 | S |
| 39PUFF | 20 | 5'-ATGTTATCC-3' | 1593 | A |
| B3-1990 | 20 | 5'-GGCTTTCCA-3' | 1990 | S |
| ID3 | 21 | 5'-CACGCCACG-3' | 2601 | S |
| B3-2689 | 22 | 5'-ACTCGGTGA-3' | 2689 | A |
| B3-2729 | 20 | 5'-ATCACCCAT-3' | 2729 | A |
| B3-AS/Spe I | 23 | 5'-GTTATAACT-3' | 2806 | S |
| AS/20(3324)S | 28 | 5'-GGCGCTTTT-3' | 3296 | S |

TABLE 1-continued

Primers used for the amplification and sequencing of CVB3

| Name | Length | Sequence (first 9 bases) | Location[a] | Orientation[b] |
|---|---|---|---|---|
| B3-3324 | 20 | 5'-ACTGCCCCT-3' | 3324 | A |
| 20/ApaL I | 22 | 5'-CCCGTTGTG-3' | 3477 | A |

[a]Numbered from the 5' terminus relative to the CVB3/20 genome (Tracy et al., 1992, supra).
[b]S, sense; A, antisense.

The B3-CO/Sac I primer was designed to incorporate the SacI restriction site (nt 751) into the CVB 3/CO VP4 coding sequence and substituted 742G3A, 748G3A, and 751 A3T without altering the amino acid sequence. Primers B3-1464, B3-1990, and B3-3324 used for RT-PCR and sequencing were designed based on published CVB3 sequences. Primers B3-1226CC, B3-2689, and B3-2729 were designed based on the consensus sequence of multiple clinical CVB3 isolates. Primers B3-AS/Spe L, AS/20(3324)S, and 20/ApaL I were designed to incorporate the entire CVB31AS capsid coding region in the CVB3/20 background using overlapping PCR products (see below).

Extraction and RT-PCR of clinical CVB3 isolates. The CVB3/CO and CVB3/AS RNA genome was extracted from 100 µl of a previously aliquoted virus stock preparation using the Isoquick (ORCA Research Inc., Bothel, Wash.) guanidinium isothiocyanate kit as specified by the manufacturer. The precipitated nucleic acid was washed in 70% ethanol and dried.

High-fidelity RT-PCR was carried out in duplicate. Following RT-PCR, duplicate reactions were pooled, loaded in 1 to 3% low-melting-point agarose gels (Agarose SF; Amresco, Solon, Ohio) containing ethidium bromide (0.5 µg/ml), and electrophoresed at 80 to 120 V in 13 Tris-acetate-EDTA) buffer for approximately 1 h. Appropriate-sized DNA bands were identified, excised from the gel, purified, and resuspended in sterile H2 O. The purified amplification products were stored at 220 C until needed.

Sequencing of RT-PCR products and cloned amplicons. Direct sequencing of RT-PCR products and clones was performed using the ThermoSequenase (Amersham, Cleveland, Ohio) terminator cycle sequencing protocol according to the manufacturer's instructions.

Samples were electrophoresed through 8% Page Plus (Amresco) gels in 0.63 glycerol tolerant buffer (1.78 M Tris-HCl, 0.57 M taurine, 0.01 M EDTA z Na$_2$ z H2 O) (U.S. Biochemical, Cleveland, Ohio) for periods of 1.5 to 6.5 h at 85-W constant power. Gels were transferred to Whatman paper and dried. Autoradiography was performed by exposure to film (Kodak/IBI, Rochester, N.Y.) for 12 to 36 h. Sequence analysis was performed with the MacVector software (version 6.0) (Kodak/IBI) and the Wisconsin Sequence Analysis Package (version 10.0) (Genetics Computer Group, Inc., Madison, Wis.).

Construction and generation of recombinant viruses. RT-PCR products generated from CVB3/CO and CVB3/AS RNA templates were blunt-end cloned into the SmaI site of pCR-Script SK(1) (Stratagene, La Jolla, Calif.) as instructed by the manufacturer. Each clone was sequenced entirely to verify its fidelity to the directly sequenced RT-PCR products. All infectious cDNA genomic constructs were verified by restriction endonuclease mapping and sequence analysis. The cDNA copy of the cardiovirulent CVB3/20 genome in the modified plasmid pSVN, and the cloned 5'NTR and capsid coding sequences of the noncardiovirulent CVB3/CO and cardiovirulent CVB3/AS clinical isolates were used to generate full-length infectious intratypic chimeras.

The complete capsid coding region (nt 743 to 3296 relative to the CVB3/20 genome) of CVB3/CO was constructed using overlapping subcloned fragments spanning the primer pairs B3-3324 B3-1464 and B3-2689 B3-CO/Sac I using the AlwNI (nt 2153) restriction site. The capsid coding region of CVB3/20 was replaced with that of CVB3/CO by exchange of the homologous SacI (nt 751)-to-AflIII (nt 3109) fragment which excludes only a single deduced amino acid difference between these strains (CVB3/20 R1264 3CVB3/CO Q).

The complete capsid coding region of CVB3/AS was generated using overlapping subcloned fragments spanning the primer pairs JRp577 39PUFF, B3-1226-CC B3-2729, and B3-3324 B3-1990, using the NsiI (nt 1291) and XmnI (nt 2649) restriction sites. To generate a full-length chimera encompassing the complete capsid sequence of CVB3/AS, PCR fragments containing CVB3/AS sequences from nt 2806 to 3304, which included the SpeI (nt 2813) site, and CVB3/20 sequences from nt 3305 to 3477, which included the ApaLI (nt 3466) site, were amplified, overlapped, and cloned by the method of Ho et al. (17) with the following modifications. Briefly, a CVB3/AS sequence specific PCR fragment spanning nt 2806 to 3324 (primer pair B3-AS/Spe I B3-3324) and a CVB3/20 sequence-specific PCR fragment spanning nt 3296 to 3477 [primer pair AS/20(3324)S 20/ApaL I] were used as template to generate the overlap PCR product described above. The entire capsid coding region of CVB3/20 was replaced with that of CVB3/AS by exchange of the SacI (nt 751)-to-SpeI (nt 2813) fragment of the CVB3/AS capsid clone plus the SpeI-to-ApaLI (nt 3466) fragment of the AS/20 overlap PCR product clone.

The 5'NTR of CVB3/CO was amplified using the primer pair JRp64-JRpATG (Romero & Rothbart, J. Virol. 69: 1370-1375, 1995). The 5'NTR of CVB3/AS was amplified using the primer pair T1-JRpATG. Both 5'NTRS were cloned as described previously and used to replace the homologous region of CVB3/20 between nt 69 and 751, using the conserved KpnI and SacI restriction sites, respectively.

Virus was generated from cDNA genomes by electroporation of 20 mg of plasmid DNA into approximately $2 \times 10^6$ HeLa cells. Cells were incubated at 37° C. and 5% $CO_2$ for 3 days or until cytopathic effect (CPE) was observed and then were thrice frozen and thawed. Viral progeny were clarified by centrifugation at 3,000×g, and 500 µl of supernatant was added to $10^6$ HeLa cells and incubated until complete CPE was observed.

Viral titer was determined using 96-well plates (Becton Dickinson, Franklin Lakes, N.J.) with $10^3$ HeLa cells/well. Samples were serially diluted to $10^{-8}$, added to the appropriate wells, incubated at 37° C. and 5% $CO_2$ for 5 days, and scored for the presence of complete CPE. $TCID_{50}$ calculations were determined.

Viral replication in cell culture. HeLa monolayers of $2 \times 10^5$ cells in 35-mm$^2$ plates (Corning, Acton, Mass.) were washed once with phosphate-buffered saline, infected at an MOI of 10 $TCID_{50}$/cell in a volume of 500 µl, and allowed to adsorb for 30 min at room temperature. Plates were then washed twice with phosphate-buffered saline to remove unbound virus, re-fed with 2 µl of supplemented MEM, incubated at 37° C. and 5% $CO_2$, and, at the given intervals, removed and frozen. Plates were thrice frozen and thawed, and 1 µl was transferred to a microcentrifuge tube and clarified by centrifugation. Viral titer was again determined.

Determination of viral cardiovirulence phenotype in mice. Groups of five juvenile (21 to 25 days of age) C3H/HeJ male mice (Jackson Laboratory, Bar Harbor, Me.) were inoculated intraperitoneally with $2 \times 10^5$ to $5 \times 10^5$ TCID$_{50}$ of virus in 0.1 ml of unsupplemented MEM or with medium alone (negative control) as described previously (e.g., Tracy et al., 1992, supra). Groups of mice were maintained in separate microisolators in a ventilated containment facility. Ten days postinoculation (dpi), mice were sacrificed and hearts were excised. One half of each heart was fixed in buffered formalin, embedded in paraffin, and sectioned. Three to six heart sections (6 mm) were stained with hemotoxylin and eosin and examined by light microscopy for evidence of myocarditis. The myocarditis lesion score of each group was determined according to the following scale: 0, no myocarditis; 1, 1 to 10 lesions per section; 2, 11 to 20 lesions per section; 3, 21 to 40 lesions per section; and 4, widespread and confluent inflammation.

Approximately one quarter of each heart was weighed and homogenized in 400 μl of supplemented MEM using a Dounce homogenizer (Fisher Scientific, Pittsburgh, Pa.). Following centrifugation (12,000×g) to clarify the remaining cellular debris, 200 μl of the supernatant was used to determine cardiac viral titers. Titers from homogenized heart were performed (see above) and expressed as log TCID50 per gram of heart tissue. RT-PCR was performed with 100 μl from each of two homogenized cardiac specimens from each group exhibiting inflammatory lesions; these reaction products were directly cycle sequenced (see above) to verify the infecting genotype. Nucleotide sequence accession numbers. GenBank accession numbers of the 5'NTRs and capsid protein coding sequences are AF169665 and AF169666 for CVB3/CO and AF169670 and AF169671 for CVB3/AS.

Results

Nucleotide analysis of the 5'NTR. There are currently five full-length infectious CVB3 cDNA clones for which complete genomic sequence data are available. These include four cardiovirulent strains and one artificially attenuated noncardiovirulent strain. Nucleotide sequence analysis indicates that all five are highly related (Romero et al., p. 97-152 in *The Coxsackie B Viruses*, S. Tracy, N. Chapman, & B. Mahy, eds., Springer-Verlag, Berlin, 1997). Several of these CVB3 strains have been used to examine the viral genetics of cardiovirulence, revealing major determinants in the 5'NTR (Lee et al., J. Med. Virol. 52: 341-347, 1997; Tu et al., J. Virol. 69: 4607-4618, 1995) and capsid coding region (Knowlton et al., J. Virol. 70: 7811-7818, 1996).

The 5'NTR nucleotide sequences of the noncardiovirulent CVB3/CO and cardiovirulent CVB3/AS strains were determined, and are set forth below as SEQ ID NO:6 and SEQ ID NO:7, respectively.

CVB3/AS 5'NTR (SEQ ID NO:6):

1 agtccctttc cccaatcgta acttagaagc aacacacact gatcaatagt tagcgtggca 61 aaccagctac gttttgatcg agcacttctg ttaccccgga ctgagtatca atagactgct 121 agcgcggttg aaggagaaaa cgttcgttat ccggccaact acttcgagaa acctagtaac 181 accatggaag ttgcagagtg tttcgctcag cactacccca gtgtagatca ggtcgatgag 241 tcaccgcatt ccccacgggc gaccgtggcg gtggctgcgt tggcggcctg cccatgggaa 301 acccatggga cgctcttata cagacatggt gcgaagagtc tattgagcta gttggtattc 361 ctccggcccc tgaatgcggc taatcctaac tgtggatcat gcgccctcaa accagaggga 421 agcgtgtcgt aatgggcaac tccgcagcgg aaccgactac tttgggtgtc cgtgtttcat 481 tttattctta ctttggctgc ttatggtgac aattgaaagg ttgttaccat atagctattg 541 gattggccat ccggtgacaa acagagctat catatatctc ttcgtagggt ttgtaccact 601 tagcttgaaa gaggtcaaga cattgcaatt cattatccaa ttgaacacag caaa

CVB3/CO 5'NTR (SEQ ID NO:7):

1 caattccctc ccttctttga aacttagaag caagcaagat aagacggtcg acaggcgaca 61 cagcaaacca gctgtgtcta gaccaagcac ttctgtgacc ccggactgag tatcaatagg 121 ctgctcgcgc ggctgaagga gaaaccgtcc gttatccggc caactacttc gagaaaccca 181 gtaacatcat ggacgttgca gagcgtttcg ctcaacactt cccccgtgta gatcaggtcg 241 atgagtcacc gctttcccca cgggcgaccg tggcggtggc tgcgttggcg gcctgcctgt 301 gggggcaccc acaggacgct ctaatacaga catggtgcga agagtctatt gagctagttg 361 gtagtcctcc ggcccctgaa tgcggctaat cctaactgcg gagcatgcac ccacaagcca 421 gtgggtagcg tgtcgtaacg ggcaactctg cagcggaacc gactactttg ggtgaccgtg 481 tttcttttta ttctctcatt ggctgcttat ggtgacaatt gaggaattgt taccatatag 541 ctattggatt ggccatccgg tgtctaacag agcaattgtt tatctgtttg tcggctttgt 601 gtctttgaac ttcaagaatt ataaaactct cgacttcata ctagagttaa actcaataag The 5' NTR of CVB3/AS and CVB3/CO were compared to the full-length CVB3 cDNA clones to examine genotypic diversity and the significance of the 5'NTR in the determination of CVB3 cardiovirulence phenotype. The 5'NTR sequences of multiple clinical CVB3 strains including CO and AS have been examined (Chapman et al., J. Med. Virol. 52: 258-261, 1997; Romero et al., 1997, supra). The CVB3/AS 5'NTR spanning nt 87 to 742 (relative to CVB3/20 genome) displayed a significantly higher nucleotide identity (90.9 to 92.3%) with the CVB3/20, CVB3/0, CVB3/Nancy, CVB3/H3, and CVB3/M strains than did the noncardiovirulent CVB3/CO 5'NTR (83.9 to 84.3%). Among themselves, CVB3/AS and CO exhibited 82.9% nucleotide identity within the 5'NTR.

Sequence identities differed significantly among the three CVB3 strains used in this study in upstream and downstream sequences of the 5'NTR comprised by nt 88 to 181 and nt 452 to 742, respectively. CVB3/CO displayed 61.6 and 62.6% nucleotide identity with the myocarditic CVB3/AS and CVB/20 strains, respectively, in the upstream region. For the same region, CVB3/AS and CVB3/20 were 85.1% identical among themselves. For sequences preceding and up to the coding start site (nt 452 to 742), CVB3/20 and CVB3/AS were 89.7% identical. CVB3/CO was only 80.3 and 82.1% identical to CVB3/AS and CVB3/20, respectively, in this same region. Analysis of the intervening sequences of the 5'NTR revealed that all three CVB3 shared between 91.8 and 97.0% nucleotide identity.

Nucleotide and amino acid analysis of the capsid coding region. The capsid nucleotide and deduced amino acid sequences of CVB3/CO and CVB3/AS were examined and compared to the homologous region of the full-length CVB3 cDNA clones to assess differences which might affect the cardiovirulence phenotype. Nucleotide analysis of the entire P1 coding region showed that CVB3/CO and CVB3/AS exhibited 79.5% nucleotide identity among themselves. The CVB3/20 strain shared 79.6 and 87.5% nucleotide identity with CVB3/CO and CVB3/AS, respectively. In fact, capsid nucleotide sequence analysis indicated that CVB3/AS and all full-length sequenced CVB3 strains clustered within the same genotypic group, while CVB3/CO fell into a separate genotype. Comparison of the deduced capsid amino acid sequences of CVB3/AS and CVB3/CO with those of the full-length sequenced CVB3 genomes showed that all strains shared greater than 97% identity (Table 2). The vast majority of nucleotide differences occurred at second- and third-base codon positions leaving the amino acid sequence unaffected.

TABLE 2

Capsid amino acid differences among CVB3 isolates

| Protein | Amino acid position[a] | Amino acid at that position in strain[b]: | | | | | |
|---|---|---|---|---|---|---|---|
| | | AS | CO | 20 | N | 0 | H3 | M |
| VP4 | 4016 | G | G | R | R | G | G | G |
| | 4018 | S | N | N | N | N | N | N |
| | 4030 | I | I | I | I | V | I | I |
| | 4042 | N | T | N | N | N | N | N |
| | 4047 | A | A | T | T | T | T | T |
| | 4051 | G | G | G | G | G | S | S |
| VP2 | 2013 | V | V | V | A | A | V | V |
| | 2045 | S | N | S | S | S | S | S |
| | 2108 | I | I | V | V | V | I | I |
| | 2138* | D | D | D | D | D | N | N |
| | 2144* | A | E | A | A | A | A | A |
| | 2151* | S | A | S | T | S | S | S |
| | 2171 | V | A | V | V | V | V | V |
| | 2179 | V | I | V | V | V | V | V |
| | 2245 | V | V | V | V | V | I | I |
| VP3 | 3046 | I | I | I | I | I | I | V |
| | 3058* | I | I | V | V | V | V | V |
| | 3062* | I | V | V | V | V | V | V |
| | 3078 | S | T | S | S | S | S | S |
| | 3155 | V | V | V | I | V | V | V |
| | 3178 | Y | Y | F | F | Y | Y | Y |
| | 3234* | Q | Q | Q | Q | E | Q | Q |
| | 3237* | F | L | F | F | F | F | F |
| VP1 | 1007 | V | I | I | I | I | I | I |
| | 1045 | S | G | G | G | G | S | S |
| | 1064 | V | I | I | I | I | I | I |
| | 1080* | E | E | K | K | E | E | E |
| | 1084 | A | S | A | A | A | A | A |
| | 1085* | K | N | K | K | K | K | K |
| | 1092 | I | I | L | L | L | I | I |
| | 1094 | P | T | P | P | P | P | P |
| | 1098 | A | V | A | A | A | A | A |
| | 1110 | V | M | V | V | V | V | V |
| | 1180 | I | I | I | I | I | V | V |
| | 1200* | S | A | S | S | S | S | S |
| | 1223* | T | A | A | A | A | A | A |
| | 1264* | Q | Q | R | Q | Q | Q | Q |

[a]Amino acid position relative to the CVB3/20 strain. Surface-exposed residues of CVB3/M determined by X-ray crystallography are marked with asterisks.
[b]Data for strains N, 0, H3, and M are from the following references, respectively: Klump et al., J. Virol. 64: 1573-1583, 1990; Chapman et al., Arch. Virol. 135: 115-130, 1994; Knowlton et al., J. Virol. 70: 7811-7818, 1996; and Lee et al., Virus Res. 50: 225-235, 1997.

Cardiovirulence phenotype and cardiac viral titers of chimeric CVB3. The full-length infectious clone of CVB3/20 has been characterized and used previously to examine determinants of cardiovirulence (Tu et al., 1995, supra). Typically, at 10 dpi, CVB3/20 induces widespread inflammatory lesions with significant necrosis and calcification in the hearts of C3H/HeJ mice. Infectious CVB3/20 was readily detectable in murine hearts at 10 dpi. The cardiovirulence phenotypes of CVB3/AS and CVB3/CO have been defined previously in C3H/HeJ and CD-1 mice (Chapman et al., 1997, supra; Gauntt & Pallansch, Virus Res. 41: 89-99, 1996; Tracy & Gauntt, Eur. Heart J. 8 (Supp 3): 445-448, 1987). CVB3/AS was cardiovirulent for adolescent (4- to 6-week-old) male and female CD-1 mice, with detectable virus in the murine myocardium at 7 dpi. CVB3/AS was also found to induce inflammatory lesions and muscle damage in hearts of 3- to 4-week-old male C3H/HeJ mice 10 dpi (Chapman et al., 1997, supra). No myocarditic lesions were observed following inoculation of CVB3/CO in male or female CD-1 or C3H/HeJ mice (Chapman et al., 1997, supra; Tracy & Gauntt, 1987, supra).

Chimeric CVB3 (FIG. 5) viruses were generated and inoculated into juvenile C3H/HeJ male mice to examine whether the 5' NTR and/or capsid coding region contained sequences that significantly influenced CVB3-induced inflammatory heart disease. To assess the role of the capsid proteins of CVB3 strains in determining the cardiovirulent phenotype, the capsid coding region of the noncardiovirulent CVB3/CO strain was used to replace the homologous region of the full-length infectious clone of the cardiovirulent CVB3/20 strain. The resultant CVB3 chimera (COP 1/20) retained the cardiovirulence phenotype of CVB3/20 in mice. Similarly, the myocarditic phenotype of CVB3/20 was not altered when the capsid coding region was exchanged for that of the cardiovirulent CVB3/AS strain (ASP 1/20). Virus was detectable in murine hearts 10 days after inoculation of strains COP1/20 and ASP 1/20 (FIG. 5).

The 5'NTRs of CVB3/CO and CVB3/AS were then examined to determine their effects, alone and in combination with their corresponding capsid coding regions, on the cardiovirulence phenotype. The 5'NTR (spanning nt 88 to 742) of CVB3/20 was replaced with that from CVB3/CO. Examination of the murine myocardium following inoculation of the resultant chimera (CO59/20) revealed no evidence of myocarditis. Similarly, when the CVB3/CO 5'NTR and capsid coding region were combined to replace the homologous regions of CVB3/20 (CO59P1/20), no myocarditic lesions were found. Ten days following inoculation of CO59/20 or CO59P1/20, detectable virus was not recovered from murine hearts by infectious assay (FIG. 5). In contrast, when the CVB3/AS 5'NTR (nt 71 to 742) alone or in combination with the AS capsid coding region was used to replace the homologous regions of CVB3/20 (AS59/20 and AS59P1/20, respectively), inflammatory lesions and significant necrosis were observed. Cardiac viral titers were obtained following inoculation of AS59/20 and AS59P1/20 (FIG. 5).

RT-PCR amplification and direct cycle sequencing of viral RNA from homogenized cardiac specimens from two separate animals of each group of mice exhibiting inflammatory heart lesions was performed. Sequence analysis of nt 630 to 850 (relative to the CVB3/20 genome) demonstrated that the infecting genotype was as had been cloned in this region and that no mutations had occurred in or around the SacI restriction site (nt 751) utilized for homologous exchange of the 59 NTR and/or capsid coding region.

Figure 6:
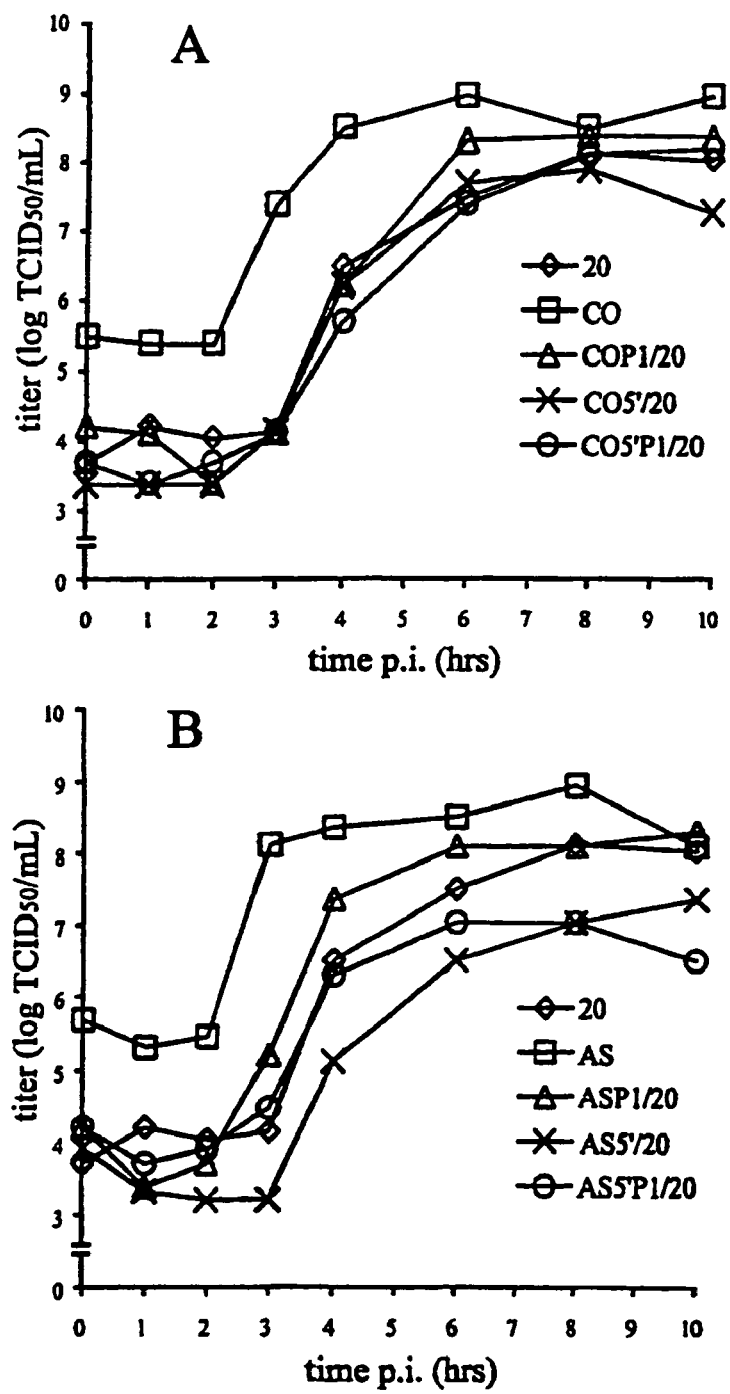
FIG. 6. One-step growth curves of parental and chimeric viruses in HeLa cells.

Growth kinetics of parental and recombinant viruses. The single-step growth characteristics of the chimeric CVB3 were examined in HeLa cells and compared to those of the parental CVB3/20, CVB3/CO, and CVB3/AS strains (FIG. 6). All parental and recombinant viruses replicated efficiently in HeLa cell cultures. All strains exhibited logarithmic growth by 3 to 4 h postinfection, and maximum titers were achieved after 6 to 8 h of incubation. While differences were observed in the duration of the lag phase (~1 h) and overall virus yield (~1 log $TCID_{50}$/ml), these did not appear to correlate with differences in myocarditic phenotype. The data indicated that homologous exchange of CVB3 59 NTR and capsid coding region between various strains resulted in viable progeny with similar replication phenotypes in HeLa cells.

Example 3

Sequences Containing the Predicted Stem Loop II Domain of Clinical Coxsackievirus B3 Isolates Determine Cardiovirulence Phenotype In this example, the sequence diversity within the 5'NTR of the phenotypically and genotypically distinct naturally occurring CVB3 strains described above was analyzed and used to identify regions for the construction of intra-5'NTR recombinants to further map the natural determinants of cardiovirulence phenotype. The sequences comprising a predicted RNA stem loop region located near the 5'-end of the viral genome were found to significantly influence CVB3-induced inflammatory heart disease and productive viral infection in murine cardiac-derived cells.

Materials and Methods

Cells and Viruses. HeLa cells (American Type Culture Collection, Manassas, Va.) and primary murine fetal heart fibroblasts (MFHF) were maintained as monolayers in minimal essential medium (MEM) supplemented with 10% (vol/vol) fetal calf serum, 2 mM L-glutamine, 25.5 mM sodium bicarbonate, and 50 µg gentamicin/mL. The cardiovirulence phenotypes of the CVB3/AS and CVB3/CO strains have been previously characterized (see above). The complete sequence and characterization of the full-length infectious cDNA clone of CVB3/20 has been described previously (Tracy et al., 1992, supra). Aliquots of low-passage viral stocks were obtained by inoculation of nearly confluent HeLa cell monolayers at an MOI of 0.5 to 1 tissue culture infective doses ($TCID_{50}$) per cell and stored at –80° C.

Construction and generation of intratypic CVB3 chimeras. The cDNA copy of the cardiovirulent CVB3/20 genome has been used (e.g., Example 2) to generate full-length infectious intratypic chimeras containing the 5'NTR and/or capsid coding sequences of the noncardiovirulent CVB3/CO or cardiovirulent CVB3/AS clinical isolates. The chimeric clone CVB3/CO5'P1/20 contains nt 88 to 3109 of CVB3/CO in the background of CVB3/20. CVB3/AS5'P1/20 contains nt 72 to 3296 of CVB3/AS in the CVB3/20 background.

Additional chimeras of the CVB3/CO and CVB3/20 5'NTR were constructed, to further localize the cardiovirulence determining region within the SLII-SLI/II linker. These chimeras comprised the following 5'NTR modifications, in the CVB3/20 background: (1) replacement of upper SLII (nts 140-180) with the corresponding region of CVB3/CO 5'NTR; (2) replacement of SLII (nts 108-188) with the corresponding region of CVB3/C0 5'NTR, leaving in place the SLI/II linker of CVB3/20; and (3) replacement of SLI-II linker (nts 88-107) with the corresponding region of CVB3/CO.

Homologous exchange of sequences within the 5'NTR was performed using conserved restriction endonuclease cleavage sites and modified PCR overlap mutagenesis. Nucleotides 88 to 181 (all nucleotide designations are relative to the CVB3/20 genome) of the CVB3/CO 5'NTR were amplified using the primer pair JRp64 and CO/180 as (33 nt, the first 9 being 5'-CTATTGATA-3'). In a subsequent PCR, using primers JRp64 and JRpATG, this CVB3/CO amplicon was fused to an upstream amplicon containing either CVB3/20 5'NTR sequences generated from the CVB3/20 clone using the primer pair 20/180s (34 nt, the first 9 being 5'-CCCGGGACT-3') and ATG or CVB3/AS 5'NTR sequences generated using the primer pair AS/180s (33 nt, the first 9 being 5'-CCCG-GACTG-3') and JRp ATG from the CVB3/AS5'P1/20 clone. Nucleotides 21 to 181 of CVB3/AS and CVB3/20 were amplified from a clone of the CVB3/AS 5'NTR (nt 21 to 742) and the CVB3/20 clone, respectively, using the primer pair T1 (Example 2) and AS/180 as (34 nt, the first 9 being 5'-CTAT-TGAT-3'). In a subsequent PCR using the primers T1 and JRpATG, this amplicon was fused to one containing CVB3/CO 5'NTR sequences generated using the primer pair CO/180s (34 nt, the first 9 being 5'-CCCGGACTG-3') and ATG. The resultant amplicons spanning either the JRp64-JRpATG or T1-JRpATG primer pairs were blunt-end cloned into the Sma I restriction site of pCR-Script SK(+) (Stratagene, La Jolla, Calif.) per the manufacturer's instructions. Each clone was sequenced to verify its fidelity to the input sequences.

The cloned chimeric 5'NTRs were digested with Kpn I (nt 69) and Sac I (nt 751) and fragments ligated into one of the following appropriate plasmid cassettes: pCO(Not I-Xma I) derived from the full-length infectious CVB3/CO5'P1/20 cDNA containing viral nt 1 to 1758; pAS(Not I-Pst I) derived from the full-length infectious CVB3/AS5'P1/20 cDNA containing viral nt 1 to 2001; and p20(Not I-Xho I) derived from the full-length infectious CVB3/20 cDNA containing viral nt 1 to 2011. Full-length genomic cDNAs were constructed using fragments derived from the chimeric plasmid cassette clones digested with their corresponding flanking restriction endonucleases and ligated into the appropriate background genome. All infectious cDNA genomic constructs were verified by restriction endonuclease mapping and sequence analysis.

CVB3/AS downstream 5'NTR sequences spanning nt 466-751 (relative to the CVB3/20 genome) were used to replace the homologous region of CVB3/CO in the CVB3/CO5'P1/20 clone using the conserved restriction endonuclease sites Bsm I (nt 466) and Sac I (nt 751).

Virus was generated from cDNA genomes by electroporation of 20 µg of plasmid DNA into approximately $2\times10^6$ HeLa cells. Cells were incubated at 37° C. and 5% $CO_2$ for 3 days or until cytopathic effect (CPE) was observed and then were thrice frozen and thawed. Supernatants were clarified by centrifugation at 3,000×g. 500 µL of supernatant was added to $1\times10^6$ HeLa cells and incubated until complete CPE occurred.

Viral titer was determined using 96-well plates (Becton Dickinson, Franklin Lakes, N.J.) with $1\times10^3$ HeLa cells/well. Samples were serially diluted to $10^{-8}$, added to the appropriate wells, incubated at 37° C. and 5% $CO_2$ for 5 days and scored for the presence of complete CPE. $TCID_{50}$ calculations were determined.

Sequencing of RT-PCR products and cloned amplicons. Direct sequencing of RT-PCR products and clones was performed using the ThermoSequenase (Amersham, Cleveland, Ohio) terminator cycle sequencing protocol as previously reported. Sequence analysis was performed using the MacVector software (version 6.0; Kodak/IBI) and the Wisconsin Sequence Analysis Package (version 10.0) (Genetics Computer Group, Inc., Madison, Wis.).

Determination of viral cardiovirulence phenotype in mice and cardiac viral titers. Groups of five juvenile (21 to 25 days of age) C3H/HeJ male mice (Jackson Laboratory, Bar Harbor, Me.) were inoculated intraperitoneally (ip) with $5\times10^5$ $TCID_{50}$ virus in 0.1 mL of unsupplemented MEM or with medium alone (negative control). Groups of mice were maintained in separate microisolators in a ventilated containment facility. Ten days post inoculation (dpi) mice were sacrificed, hearts were excised, and examined for evidence of myocarditis. The myocarditis lesion score of each group was determined according to the following scale: 0, no myocarditis; 1, 1 to 10 lesions per section; 2, 11 to 20 lesions per section; 3, 21 to 40 lesions per section; and 4, widespread and confluent inflammation.

Approximately one quarter of each heart was homogenized and used to determine cardiac viral titers. Titration of viral concentration from homogenized heart tissue was performed as described above and expressed as log $TCID_{50}$ per gram of tissue.

Viral replication in cell culture. HeLa cell and MFHF monolayers of $2 \times 10^5$ cells or $5 \times 10^4$ cells, respectively, in duplicate 35 mm² plates (Corning, Acton, Mass.) were washed once with phosphate buffered saline, infected at a MOI of 10 $TCID_{50}$ cell in a volume of 500 μL and allowed to adsorb for 30 min. at room temperature. Plates were then washed twice with phosphate buffered saline to remove unbound virus, refed with 2 mL of supplemented MEM and incubated at 37° C. or 33.5° C. and 5% $CO_2$. At the given intervals plates were thrice frozen and thawed, 1 mL transferred to a microcentrifuge tube and clarified by centrifugation. Viral titer was determined as described above.

Extraction and amplification of viral genomes from cardiac samples. From each group of inoculated mice, two homogenized cardiac samples were used for RT-PCR amplification of the viral genome and direct sequencing of the 5'NTR. Total nucleic acid was extracted from 100 μL of each homogenized cardiac sample using guanidinium isothiocyanate (Isoquick, ORCA Research Inc., Bothel, Wash.), precipitated, washed in 70% ethanol and dried. High fidelity RT-PCR was carried out as described in Example 2 using the primer pairs JRp64/MD90, MD91/JRpATG, and JRp577/3'PUFF. Detected amplicons were purified and directly cycle sequenced to verify the fidelity of the infecting genotype 5'NTR and, in some instances, partial capsid sequences.

Computer analysis of secondary RNA structures. The RNA secondary structures of the sequences spanning nt 88 to 181 of CVB3/20 and CVB3/AS and nt 88 to 186 of CVB3/CO were predicted using the Wisconsin Sequence Analysis Package (version 10.0) (Genetics Computer Group, Inc., Madison, Wis.) Mfold program version 2.3 and the on-line Mfold server at www.ibc.wustl.edu/~zuker/rna/form1.cgi. The default parameters (37° C., 1 M NaCl, no divalent ions, and 5% suboptimality) and the energy parameters given by Mathews et al. were used for the predictions (Mathews et al. J. Mol. Biol. 288: 911-940, 1999).

Results

5'NTR nucleotides 88 to 181 determine CVB3 cardiovirulence phenotype. Sequence analysis of the 5'NTR revealed that nucleotide identities differed significantly among the three CVB3 strains in upstream and downstream regions comprised by nucleotides 88 to 181 and nucleotides 452 to 742 (all numeration relative to CVB3/20), respectively. Within the upstream region, the noncardiovirulent CVB3/CO strain displayed 62 and 63% identity with the myocarditic CVB3/AS and CVB3/20 strains, respectively. For the same region, CVB3/AS and CVB3/20 were 85% identical. Within the upstream region, CVB3/CO was found to possess 5 additional nucleotides compared to the other 2 strains. For the region spanning nucleotides 452 to 742, CVB3/20 and CVB3/AS were 90% identical. CVB3/CO shared 80 and 82% identity with CVB3/AS and CVB3/20, respectively, in this region. Analysis of the intervening sequences of the 5'NTR (nucleotides 182 to 451) revealed that all 3 strains shared between 92 and 97% identity.

Based on the 5'NTR sequence analysis, a panel of intra-5'NTR CVB3 chimeras were generated to determine whether the identified regions of nt diversity contained the primary determinant of cardiovirulence. The downstream nucleotides 452 to 742 from CVB3/AS were used to replace the homologous region of a noncardiovirulent chimera, CVB3/CO$_5$'P1/20 (as described in Example 2), containing the CVB3/CO 5'NTR and capsid coding sequences in the CVB3/20 background. The resultant virus, CVB3/AS(BsmI-ATG)/CO/20, retained a noncardiovirulent phenotype when inoculated into juvenile male C3H/HeJ mice. The contribution of upstream 5'NTR sequences (nucleotides 88 to 181) on cardiovirulence phenotype were explored by homologous exchange of that region in the cardiovirulent CVB3/20 and CVB3/AS5'P1/20 (Example 2) viruses by sequences from the noncardiovirulent CVB3/CO isolate, CVB3/COSL2/20 and CVB3/COSL2/AS/20, respectively. For CVB3/COSL2/AS/20, the cardiovirulent phenotype was found to be completely abrogated in all mice inoculated. No virus was detected in the hearts of these mice by infectious assay or RT-PCR. Similarly, inoculation of CVB3/COSL2/20 into mice resulted in nearly abrogation of the parental cardiovirulent phenotype. One of five mice inoculated with CVB3/COSL2/20 did exhibit modest myocardial inflammatory disease compared to positive controls. A low titer (3.9 log $TCID_{50}$ of virus per gram of heart tissue) was recovered from this sole heart in an infectious assay. RT-PCR amplification of this homogenized heart tissue detected the presence of viral genome. Direct sequencing of nucleotides 88 to 576 within the 5'NTR demonstrated that no mutations had occurred that could explain the low-level cardiovirulence. From the remaining mice inoculated with CVB3/COSL2/20, no viable virus was recovered from the homogenized myocardium by infectious assay, nor was viral genome detected by RT-PCR.

Two additional intratypic CVB3 chimeras were generated to confirm that nucleotides 88 to 181 contained the major determinant of cardiovirulence. As previously reported, the noncardiovirulent chimera CVB3/CO$_5$'P1/20 was consistently unable to induce acute myocardial damage in a murine model. Furthermore, no infectious virus could be recovered from hearts of mice inoculated with this chimera. When nucleotides 88 to 186 contributed by the noncardiovirulent CVB3/CO strain of this recombinant virus were replaced by homologous sequences from either CVB3/20 or CVB3/AS, chimeras CVB3/20SL2/CO/20 and CVB3/ASSL2/CO/20 respectively, the noncardiovirulent phenotype converted to one of cardiovirulence. In addition, following inoculation of these chimeras, virus was recovered from the myocardium of all mice tested. RT-PCR amplification and direct sequencing of 5'NTR nucleotides 88 to 742 of the myocardium-derived viruses demonstrated they were identical to that of the inoculum. Thus, within this portion of the 5'NTR, no mutations had occurred during replicative infection in mice.

CVB3 replication in cardiac-derived cells correlates with cardiovirulence phenotype. The growth characteristics of parental and intra-5'NTR recombinant CVB3 were examined in HeLa and primary murine derived fetal heart fibroblast (MFHF) cell cultures. Both noncardiovirulent and cardiovirulent viruses replicated efficiently and with similar growth kinetics in HeLa cells. In contrast, only those strains found to induce inflammatory heart lesions in mice were capable of robust growth in MFHF at 37° C.

Noncardiovirulent CVB3 strains displayed a temperature sensitive growth phenotype in MFHF. While limited or no growth was observed at 37° C., the amyocarditic strains were found to replicate as well as cardiovirulent viruses when incubated at 33.5° C. The growth kinetics of CVB3/20 were efficient at both temperatures.

Predicted RNA secondary structure of 5'NTR nucleotides 88 to 181-186. To assess the contribution RNA secondary structure might play in determining CVB3 cardiovirulence phenotype, nt 88 to 181 of CVB3/AS and CVB3/20 and nt 88 to 186 of CVB3/CO, which include the putative SLI-II linker sequences and SLII, were analyzed using the Mfold algorithm. Computational folding predicted a single possible optimum pattern for CVB3/AS and CVB3/20 nucleotides 88 to 181 (FIG. 7). Although the cardiovirulent CVB3/AS and CVB3/20 stras shared only 85% in this region, the predicted RNA secondary structures were nearly identical. Nucleotides 88 to 104 (the putative SLI-II linker region) of these two strains was predicted to be single-stranded. The lower stem region was comprised of 10 and 11 paired bases for CVB3/20 and CVB3/AS, respectively. Both contained a UU bulge at the same location within this lower stem region. The upper stem loop region was similar, comprised of 16 and 14 paired bases for CVB3/AS and CVB3/20, respectively. Both possessed a mid-region 5 nucleotide bulge and an apical 6 nucleotide loop. The sequences comprising the apical loops differed at only one position (nt 148). The major SLII structural differences between CVB3/AS and CVB3/20 were contributed by the bulge region between the upper and lower stems. The upstream and downstream portions of the CVB3/AS bulge region were 1 and 2 nucleotide shorter, respectively, than those of CVB3/20.

The SLII region of the noncardiovirulent CVB3/CO strain differed significantly in its predicted structure compared to that of the cardiovirulent strains (FIG. 7). The optimal folding pattern of nucleotides 88 to 186 of CVB3/CO predicted the formation of 3 separate SLs. Unlike the initial 17 nucleotide single-stranded segment in cardiovirulent strains, some bases within CVB3/CO nucleotides 88 to 104 were involved in base pair interactions. As a result, the predicted inter-SL1/2 linker was significantly reduced in length (7 versus 17 nucleotides). Nucleotides 95 to 121 comprised the first SL. The second SL (nucleotides 133 to 171), separated from the first by 11 single-stranded bases, was comprised of a 4 nucleotide lower stem separated from an 8 nucleotide upper stem by a large bulge region. The upper stem was capped by an apical 6 nucleotide loop. It is interesting to note that this upper stem and loop portion is identical in structure to the homologous regions of CVB3/AS and CVB3/20. Furthermore, all strains shared a 5'-ANACCA-3' loop motif. Lastly, a minor, third SL spanned nucleotides 175 to 184 is predicted to exist.

To further validate the predicted folding pattern and assess whether the cardiovirulence determining region might alter the enteroviral cloverleaf structure, all CVB3 SLII regions were computationally folded in conjunction with the initial 87 nucleotides of CVB3/20 (present in all of the chimeric strains described). The 5'-terminal sequences formed the predicted enterovirus "cloverleaf" structure independently of the predicted folding patterns of nt 88 to 181. Furthermore, the cardiovirulence determining sequences adopted the motif described previously.

This invention is not limited to the embodiments described and exemplified above, but is capable of variation and modification within the scope of the appended claims.

We claim:

1. A coxsackievirus B3 genome for use as a vector, which is modified to produce a virus having a restricted or altered species or tissue tropism as compared with an equivalent, but unmodified virus, wherein the modification consists of replacing the Domain II and the Domain I/II linker of the 5' nontranslated region (5'NTR) of said genome with Domain II and the Domain I/II linker of the 5'NTR of a second coxsackievirus B3 genome that encodes an a second coxsackievirus B3 having the restricted or altered species or tissue tropism, thereby generating a chimeric 5'NTR;

wherein said Domain II and the Domain I/II linker corresponds to nucleotides 88-186 of the CVB3/CO 5'NTR.

2. The coxsackievirus B3 genome of claim 1, wherein said second coxsackievirus B3 is coxsackievirus B3/CO.

3. The coxsackievirus B3 genome of claim 1, which produces a noncardiovirulent coxsackievirus B3.

4. A vector for delivering a gene of interest to a target cell, the vector comprising a chimeric 5'NTR;

wherein the chimeric 5'NTR is the 5'NTR of a first coxsackievirus B3 wherein only the Domain II and the Domain I/II linker has been replaced with Domain II and the Domain I/II linker of the 5'NTR of a second coxsackievirus B3 having a restricted or altered species or tissue tropism; and wherein said Domain II and the Domain I/II linker corresponds to nucleotides 88-186 of the CVB3/CO 5'NTR.

5. The vector of claim 4, wherein the coxsackievirus B3 is selected from the group consisting of CVB3/20 and CVB3/AS.

6. The vector of claim 4, wherein the target cell is a human cell.

7. The vector of claim 6, wherein the target cell is a heart cell.

8. A recombinant coxsackievirus B3 having a genome comprising a chimeric 5'NTR;
   wherein said chimeric 5'NTR is the endogenous 5'NTR wherein only the Domain II and the Domain I/II linker is replaced with an equivalent part of a heterologous 5'NTR of a second coxsackievirus B3; and
   wherein said Domain II and the Domain I/II linker corresponds to nucleotides 88-186 of the CVB3/CO 5'NTR.

9. An avirulent coxsackievirus B3 vector comprising a coxsackievirus B3 genome and a heterologous 5'NTR polynucleotide sequence wherein the Domain II and the Domain I/II linker of the CVB3/CO 5'NTR has replaced the equivalent part of a heterologous coxsackievirus B3 5'NTR; and
   wherein said Domain II and the Domain I/II linker corresponds to nucleotides 88-186 of the CVB3/CO 5'NTR.

10. The coxsackievirus B3 vector vaccine of claim 9 wherein said coxsackievirus B3 is selected from the group consisting of CVB3/20, CVB3/AS and CVB3/CO.

* * * * *